(12) United States Patent
Giblin et al.

(10) Patent No.: US 8,026,270 B2
(45) Date of Patent: Sep. 27, 2011

(54) BENZO [F] ISOINDOLES AS EP4 RECEPTOR AGONISTS

(75) Inventors: Gerard Martin Paul Giblin, Harlow (GB); Mark Patrick Healy, Harlow (GB); Helen Susanne Price, Harlow (GB)

(73) Assignee: Glaxo Group Limited, Greenford, Middlesex (GB)

( * ) Notice: Subject to any disclaimer, the term of this patent is extended or adjusted under 35 U.S.C. 154(b) by 89 days.

(21) Appl. No.: 12/375,455

(22) PCT Filed: Jul. 26, 2007

(86) PCT No.: PCT/EP2007/057716
§ 371 (c)(1),
(2), (4) Date: Jan. 28, 2009

(87) PCT Pub. No.: WO2008/012347
PCT Pub. Date: Jan. 31, 2008

(65) Prior Publication Data
US 2009/0312388 A1    Dec. 17, 2009

(30) Foreign Application Priority Data

Jul. 28, 2006    (GB) .................................. 0615105.4

(51) Int. Cl.
*A61K 31/4035* (2006.01)
*C07D 209/80* (2006.01)
(52) U.S. Cl. ......................... 514/411; 548/450; 548/451
(58) Field of Classification Search .................. 514/411; 548/450, 451
See application file for complete search history.

(56) References Cited

FOREIGN PATENT DOCUMENTS

| WO | 0250032 A | 6/2002 |
|---|---|---|
| WO | 0250033 A | 6/2002 |
| WO | 02064564 A | 8/2002 |

*Primary Examiner* — James Anderson
*Assistant Examiner* — Zohreh Vakili
(74) *Attorney, Agent, or Firm* — Bonnie L. Deppenbrock

(57) ABSTRACT

The present invention relates to naphthalene derivatives, to processes for their preparation, to pharmaceutical compositions containing them and to their use in medicine.

8 Claims, No Drawings

BENZO [F] ISOINDOLES AS EP4 RECEPTOR AGONISTS

CROSS-REFERENCE TO RELATED APPLICATIONS

This application is filed pursuant to 35 USC 371 as a United States National Phase Application of International Patent Application Serial No. PCT/EP2007/057716 filed on Jul. 26, 2007, which claims priority from 0615105.4 filed on Jul. 28, 2006 in the United Kingdom.

FIELD OF THE INVENTION

This invention relates to naphthalene derivatives, to processes for their preparation, to pharmaceutical compositions containing them and to their use in medicine.

BACKGROUND OF THE INVENTION

The compounds of the present invention are $EP_4$ receptor agonists.

A number of review articles describe the characterization and therapeutic relevance of the prostanoid receptors as well as the most commonly used selective agonists and antagonists: *Eicosanoids; From Biotechnology to Therapeutic Applications*, Folco, Samuelsson, Maclouf, and Velo eds, Plenum Press, New York, 1996, chap. 14, 137-154 and Journal of Lipid Mediators and Cell Signalling, 1996, 14, 83-87 and *Prostanoid Receptors, Structure, Properties and Function*, S Narumiya et al, Physiological Reviews 1999, 79(4), 1193-126.

The $EP_4$ receptor is a 7-transmembrane receptor and its natural ligand is the prostaglandin $PGE_2$. $PGE_2$ also has affinity for the other EP receptors (types $EP_1$, $EP_2$ and $EP_3$). The prostanoid $EP_4$ receptor falls into a group of receptors normally associated with elevation of intracellular cyclic adenosine monophosphate (cAMP) levels. The $EP_4$ receptor is associated with smooth muscle relaxation, intraocular pressure, pain (in particular inflammatory, neuropathic and visceral pain), inflammation, neuroprotection, lymphocyte differentiation, bone metabolic processes, allergic activities, promotion of sleep, renal regulation, gastric or enteric mucus secretion and duodenal bicarbonate secretion. The $EP_4$ receptor plays an important role in closure of the ductus arteriosus, vasodepression, inflammation and bone remodeling as reviewed by Narumiya in *Prostaglandins & Other Lipid Mediators* 2002, 68-69 557-73.

A number of publications have demonstrated that $PGE_2$ acting through the $EP_4$ receptor subtype, and $EP_4$ agonists alone, can regulate inflammatory cytokines after an inflammatory stimulus. Takayama et al in the *Journal of Biological Chemistry* 2002, 277(46), 44147-54 showed $PGE_2$ modulates inflammation during inflammatory diseases by suppressing macrophage derived chemokine production via the $EP_4$ receptor. In *Bioorganic & Medicinal Chemistry* 2002, 10(7), 2103-2110, Maruyama et al demonstrate the selective $EP_4$ receptor agonist (ONO-AE1-437) suppresses LPS induced TNF-α in human whole blood whilst increasing the levels of IL-10. An article in *Anesthesiology*, 2002, 97, 170-176 suggests that a selective $EP_4$ receptor agonist (ONO-AE1-329) effectively inhibited mechanical and thermal hyperalgesia and inflammatory reactions in acute and chronic monoarthritis.

Two independent articles from Sakuma et al in *Journal of Bone and Mineral Research* 2000, 15(2), 218-227 and Miyaura et al in *Journal of Biological Chemistry* 2000, 275 (26), 19819-23, report impaired osteoclast formation in cells cultured from $EP_4$ receptor knock-out mice. Yoshida et al in *Proceedings of the National Academy of Sciences of the United States of America* 2002, 99(7), 4580-4585, by use of mice lacking each of the $PGE_2$ receptor EP subtypes, identified $EP_4$ as the receptor that mediates bone formation in response to $PGE_2$ administration. They also demonstrated a selective $EP_4$ receptor agonist (ONO-4819) consistently induces bone formation in wild type mice. Additionally, Terai et al in *Bone* 2005, 37(4), 555-562 have shown the presence of a selective $EP_4$ receptor agonist (ONO-4819) enhanced the bone-inducing capacity of rhBMP-2, a therapeutic cytokine that can induce bone formation.

Further research by Larsen et al shows the effects of $PGE_2$ on secretion in the second part of the human duodenum is mediated through the $EP_4$ receptor (*Acta. Physiol. Scand.* 2005, 185, 133-140). Also, it has been shown a selective $EP_4$ receptor agonist (ONO-AE1-329) can protect against colitis in rats (Nitta et al in *Scandinavian Journal of Immunology* 2002, 56(1), 66-75).

Doré et al in *The European Journal of Neuroscience* 2005, 22(9), 2199-206 have shown that $PGE_2$ can protect neurons against amyloid beta peptide toxicity by acting on $EP_2$ and $EP_4$ receptors. Furthermore Doré has demonstrated in *Brain Research* 2005, 1066(1-2), 71-77 that an $EP_4$ receptor agonist (ONO-AE1-329) protects against neurotoxicity in an acute model of excitotoxicity in the brain.

Woodward et al in *Journal of Lipid Mediators* 1993, 6(1-3), 545-53 found intraocular pressure could be lowered using selective prostanoid agonists. Two papers in *Investigative Ophthalmology & Visual Science* have shown the prostanoid $EP_4$ receptor is expressed in human lens epithelial cells (Mukhopadhyay et al 1999, 40(1), 105-12), and suggest a physiological role for the prostanoid $EP_4$ receptor in modulation of flow in the trabecular framework of the eye (Hoyng et al 1999, 40(11), 2622-6).

Compounds exhibiting $EP_4$ receptor binding activity have been described in, for example, WO98/55468, WO00/18744, WO00/03980, WO00/15608, WO0016760, WO00/21532, EP0855389, EP0985663, WO02/50031, WO02/50032, WO02/50033, WO02/064564, WO03/103604, WO03/077910, WO03/086371, WO04/037813, WO04/067524, WO04/085430, U.S. Ser. No. 04/142,969, WO05/021508, WO05/105733, WO05/105732, WO05/080367, WO05/037812 and WO05/116010.

Derivatives of indoprofen such as [4-(1-oxo-1,3-dihydro-2H-benzo[f]isoindol-2-yl)phenyl]-2-propionic acid, sodium salt have been described by Rufer et. al. in *Eur. J. Med. Chem.—Chimica Therapeutica*, 1978, 13, 193.

DETAILED DESCRIPTION

The present invention provides an $EP_4$ receptor agonist selected from the group consisting of:
(3-chloro-4-{1,3-dioxo-4,9-bis[(2,2,2-trifluoroethyl)oxy]-1,3-dihydro-2H-benzo[f]isoindol-2-yl}phenyl)acetic acid;
(3-chloro-4-{1-oxo-4,9-bis[(2,2,2-trifluoroethyl)oxy]-1,3-dihydro-2H-benzo[f]isoindol-2-yl}phenyl)acetic acid;
(4-{4-(ethyloxy)-1,3-dioxo-9-[(2,2,2-trifluoroethyl)oxy]-1,3-dihydro-2H-benzo[f]isoindol-2-yl}-3-fluorophenyl) acetic acid;
(3-chloro-4-{4-(ethyloxy)-1,3-dioxo-9-[(2,2,2-trifluoroethyl)oxy]-1,3-dihydro-2H-benzo[f]isoindol-2-yl}phenyl) acetic acid;
(3-chloro-4-{4-(ethyloxy)-1-oxo-9-[(2,2,2-trifluoroethyl) oxy]-1,3-dihydro-2H-benzo[f]isoindol-2-yl}phenyl)acetic acid;

(3-chloro-4-{9-(ethyloxy)-1-oxo-4-[(2,2,2-trifluoroethyl)oxy]-1,3-dihydro-2H-benzo[f]isoindol-2-yl}phenyl)acetic acid;

(4-{9-(ethyloxy)-1-oxo-4-[(2,2,2-trifluoroethyl)oxy]-1,3-dihydro-2H-benzo[f]isoindol-2-yl}-3-fluorophenyl)acetic acid;

(4-{4-(ethyloxy)-1-oxo-9-[(2,2,2-trifluoroethyl)oxy]-1,3-dihydro-2H-benzo[f]isoindol-2-yl}-3-fluorophenyl)acetic acid; or a pharmaceutically acceptable derivative thereof (hereafter 'the compounds of the invention').

By pharmaceutically acceptable derivative is meant any pharmaceutically acceptable salt, solvate or ester, or salt or solvate of such ester of the compounds of the invention, or any other compound which upon administration to the recipient is capable of providing (directly or indirectly) a compound of the invention or an active metabolite or residue thereof.

It will be appreciated that, for pharmaceutical use, the salts referred to above will be the pharmaceutically acceptable salts, but other salts may find use, for example in the preparation of compounds of the invention and the pharmaceutically acceptable salts thereof.

Pharmaceutically acceptable salts include those described by Berge, Bighley and Monkhouse, *J. Pharm. Sci.*, 1977, 66, 1-19. The term "pharmaceutically acceptable salts" refers to salts prepared from pharmaceutically acceptable bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Salts derived from pharmaceutically acceptable organic bases include salts of primary, secondary, and tertiary amines; substituted amines including naturally occurring substituted amines; and cyclic amines. Particular pharmaceutically acceptable organic bases include arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, procaine, purines, theobromine, triethylamine, trimethylamine, tripropyl amine, tris(hydroxymethyl)aminomethane, and the like. Salts may also be formed from basic ion exchange resins, for example polyamine resins.

It will be appreciated that the compounds of the invention may be produced in vivo by metabolism of a suitable prodrug. Such prodrugs may be for example physiologically acceptable metabolically labile esters of the compounds of the invention. These may be formed by esterification of the carboxylic acid group in the parent compound of the invention with, where appropriate, prior protection of any other reactive groups present in the molecule followed by deprotection if required. Examples of such metabolically labile esters include $C_{1-4}$ alkyl esters e.g. methyl ethyl or t-butyl esters esters, $C_{3-6}$ alkenyl esters e.g. allyl substituted or unsubstituted aminoalkyl esters (e.g. aminoethyl, 2-(N,N-diethylamino)ethyl, or 2-(4-morpholino)ethyl esters or acyloxyalkyl esters such as, acyloxymethyl or 1-acyloxyethyl e.g. pivaloyloxymethyl, 1-pivaloyloxyethyl, acetoxymethyl, 1-acetoxyethyl, 1-(1-methoxy-1-methyl)ethylcarbonyloxyethyl, 1-benzoyloxyethyl, isopropoxycarbonyloxymethyl, 1-isopropoxycarbonyloxyethyl, cyclohexylcarbonyloxymethyl, 1-cyclohexylcarbonyloxyethyl ester, cyclohexyloxycarbonyloxymethyl, 1-cyclohexyloxycarbonyloxyethyl, 1-(4-tetrahydropyranyloxy)carbonyloxyethyl or 1-(4-tetrahydropyranyl)carbonyloxyethyl.

It is to be understood that the present invention encompasses all isomers of the compounds of the invention and their pharmaceutically acceptable derivatives, including all geometric, tautomeric and optical forms, and mixtures thereof (e.g. racemic mixtures).

Since the compounds of the invention are intended for use in pharmaceutical compositions, it will be understood that they are each provided in substantially pure form, for example at least 50% pure, more suitably at least 75% pure and preferably at least 95% pure (% are on a wt/wt basis). Impure preparations of the compounds of the invention may be used for preparing the more pure forms used in the pharmaceutical compositions. Although the purity of intermediate compounds of the present invention is less critical, it will be readily understood that the substantially pure form is preferred as for the compounds of the invention. Preferably, whenever possible, the compounds of the present invention are obtained in crystalline form.

When some of the compounds of this invention are allowed to crystallise or are recrystallised from organic solvents, solvent of crystallisation may be present in the crystalline product. This invention includes within its scope such solvates. Similarly, some of the compounds of this invention may be crystallised or recrystallised from solvents containing water. In such cases water of hydration may be formed. This invention includes within its scope stoichiometric hydrates as well as compounds containing variable amounts of water that may be produced by processes such as lyophilisation. In addition, different crystallisation conditions may lead to the formation of different polymorphic forms of crystalline products. This invention includes within its scope all polymorphic forms of the compounds of the invention.

The present invention also includes within its scope all isotopically-labelled compounds of the invention. Such compounds are identical to those recited in the list of the compounds of the invention except that one or more atoms therein are replaced by an atom having an atomic mass or mass number different from the atomic mass or mass number usually found in nature. Examples of isotopes that can be incorporated into compounds of the invention and pharmaceutically acceptable derivatives thereof include isotopes of hydrogen, carbon, nitrogen, oxygen, fluorine and chlorine, such as 2H, 3H, 11C, 13C, 14C, 15N, 17O, 18O, 18F and 36Cl.

Isotopically-labelled compounds of the invention, for example those into which radioactive isotopes such as 3H, 14C are incorporated, are useful in drug and/or substrate tissue distribution assays. Tritiated, i.e., 3H, and carbon-14, i.e., 14C, isotopes are particularly preferred for their ease of preparation and detectability. 11C and 18F isotopes are particularly useful in PET (positron emission tomography) and are useful in brain imaging. Further substitution with heavier isotopes such as deuterium, i.e., 2H, can afford certain therapeutic advantages resulting from greater metabolic stability, for example increased in vivo half-life or reduced dosage requirements and, hence, may be preferred in some circumstances. Isotopically labelled compounds of the invention may be prepared by carrying out the synthetic procedures disclosed in the Schemes and/or in the Examples below, by substituting a readily available isotopically labelled reagent for a non-isotopically labelled reagent.

The compounds of the invention are $EP_4$ receptor agonists and may therefore be useful in treating $EP_4$ receptor mediated diseases.

In particular the compounds of the invention may be useful in the treatment of pain, for example, chronic articular pain (e.g. rheumatoid arthritis, osteoarthritis, rheumatoid spondylitis, gouty arthritis and juvenile arthritis) including the property of disease modification and joint structure preservation; musculoskeletal pain; lower back and neck pain; sprains and strains; neuropathic pain; sympathetically maintained pain; myositis; pain associated with cancer and fibromyalgia; pain associated with migraine; pain associated with influenza or other viral infections, such as the common cold; rheumatic fever; pain associated with functional bowel disorders such as non-ulcer dyspepsia, non-cardiac chest pain and irritable bowel syndrome; pain associated with myocardial ischemia; post operative pain; headache; toothache; and dysmenorrhea.

The compounds of the invention may be particularly useful in the treatment of neuropathic pain and symptoms associated therewith. Neuropathic pain syndromes include: diabetic neuropathy; sciatica; non-specific lower back pain; multiple sclerosis pain; fibromyalgia; HIV-related neuropathy; postherpetic neuralgia; trigeminal neuralgia; and pain resulting from physical trauma, amputation, cancer, toxins or chronic inflammatory conditions. Symptoms of neuropathic pain include spontaneous shooting and lancinating pain, or ongoing, burning pain. In addition, there is included pain associated with normally non-painful sensations such as "pins and needles" (paraesthesias and dysesthesias), increased sensitivity to touch (hyperesthesia), painful sensation following innocuous stimulation (dynamic, static or thermal allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

The compounds of the invention may also be useful in the treatment of inflammation, for example in the treatment of skin conditions (e.g. sunburn, burns, eczema, dermatitis, psoriasis); ophthalmic diseases such as glaucoma, retinitis, retinopathies, uveitis and of acute injury to the eye tissue (e.g. conjunctivitis); lung disorders (e.g. asthma, bronchitis, emphysema, allergic rhinitis, respiratory distress syndrome, pigeon fancier's disease, farmer's lung, COPD); gastrointestinal tract disorders (e.g. aphthous ulcer, Crohn's disease, atopic gastritis, gastritis varialoforme, ulcerative colitis, coeliac disease, regional ileitis, irritable bowel syndrome, inflammatory bowel disease, gastrointestinal reflux disease, diarrhoea, constipation); organ transplantation; other conditions with an inflammatory component such as vascular disease, migraine, periarteritis nodosa, thyroiditis, aplastic anaemia, Hodgkin's disease, sclerodoma, myaesthenia gravis, multiple sclerosis, sorcoidosis, nephrotic syndrome, Bechet's syndrome, polymyositis, gingivitis, myocardial ischemia, pyrexia, systemic lupus erythematosus, polymyositis, tendinitis, bursitis, and Sjogren's syndrome.

The compounds of the invention may also be useful in the treatment of immunological diseases such as autoimmune diseases, immunological deficiency diseases or organ transplantation. The compounds of the invention may also be effective in increasing the latency of HIV infection.

The compounds of the invention may also be useful in the treatment of diseases of excessive or unwanted platelet activation such as intermittent claudication, unstable angina, stroke, and acute coronary syndrome (e.g. occlusive vascular diseases).

The compounds of the invention may also be useful as a drug with diuretic action, or may be useful to treat overactive bladder syndrome.

The compounds of the invention may also be useful in the treatment of impotence or erectile dysfunction.

The compounds of the invention may also be useful in the treatment of bone disease characterised by abnormal bone metabolism or resorption such as osteoporosis (especially postmenopausal osteoporosis), hyper-calcemia, hyperparathyroidism, Paget's bone diseases, osteolysis, hypercalcemia of malignancy with or without bone metastases, rheumatoid arthritis, periodontitis, osteoarthritis, ostealgia, osteopenia, calculosis, lithiasis (especially urolithiasis), gout and ankylosing spondylitis, tendinitis and bursitis.

The compounds of the invention may also be useful in bone remodelling and/or promoting bone generation and/or promoting fracture healing.

The compounds of the invention may also be useful for attenuating the hemodynamic side effects of NSAIDs and COX-2 inhibitors.

The compounds of the invention may also be useful in the treatment of cardiovascular diseases such as hypertension or myocardial ischemia; functional or organic venous insufficiency; varicose therapy; haemorrhoids; and shock states associated with a marked drop in arterial pressure (e.g. septic shock).

The compounds of the invention may also be useful in the treatment of neurodegenerative diseases and neurodegeneration such as dementia, particularly degenerative dementia (including senile dementia, Alzheimer's disease, Pick's disease, Huntingdon's chorea, Parkinson's disease and Creutzfeldt-Jakob disease, ALS, motor neuron disease); vascular dementia (including multi-infarct dementia); as well as dementia associated with intracranial space occupying lesions; trauma; infections and related conditions (including HIV infection); metabolism; toxins; anoxia and vitamin deficiency; and mild cognitive impairment associated with ageing, particularly Age Associated Memory Impairment.

The compounds of the invention may also be useful in the treatment of neurological disorders and may be useful as neuroprotecting agents. The compounds of the invention may also be useful in the treatment of neurodegeneration following stroke, cardiac arrest, pulmonary bypass, traumatic brain injury, spinal cord injury or the like.

The compounds of the invention may also be useful in the treatment of complications of Type 1 diabetes (e.g. diabetic microangiopathy, diabetic retinopathy, diabetic nephropathy, macular degeneration, glaucoma), nephrotic syndrome, aplastic anaemia, uveitis, Kawasaki disease and sarcoidosis.

The compounds of the invention may also be useful in the treatment of kidney dysfunction (nephritis, particularly mesangial proliferative glomerulonephritis, nephritic syndrome), liver dysfunction (hepatitis, cirrhosis) and gastrointestinal dysfunction (diarrhoea).

It is to be understood that reference to treatment includes both treatment of established symptoms and prophylactic treatment.

According to a further embodiment of the invention, there is provided a compound of the invention or a pharmaceutically acceptable derivative thereof for use in human or veterinary medicine.

According to another embodiment of the invention, there is provided a compound of the invention or a pharmaceutically acceptable derivative thereof for use in the treatment of a condition which is mediated by the action, or loss of action, of $PGE_2$ at $EP_4$ receptors.

According to a further embodiment of the invention, there is provided a method of treating a human or animal subject suffering from a condition which is mediated by the action, or by loss of action, of $PGE_2$ at $EP_4$ receptors which comprises administering to said subject an effective amount of a compound of the invention or a pharmaceutically acceptable derivative thereof.

According to a further embodiment of the invention there is provided a method of treating a human or animal subject suffering from a pain, inflammatory, immunological, bone, neurodegenerative or renal disorder, which method comprises administering to said subject an effective amount of a compound of the invention or a pharmaceutically acceptable derivative thereof.

According to another embodiment of the invention, there is provided the use of a compound of the invention or a pharmaceutically acceptable derivative thereof for the manufacture of a medicament for the treatment of a condition which is mediated by the action of $PGE_2$ at $EP_4$ receptors.

According to another embodiment of the invention there is provided the use of a compound of the invention or a pharmaceutically acceptable derivative thereof for the manufacture of a medicament for the treatment or prevention of a condition such as a pain, inflammatory, immunological, bone, neurodegenerative or renal disorder.

The compounds of the invention and their pharmaceutically acceptable derivatives are conveniently administered in the form of pharmaceutical compositions. Such compositions may conveniently be presented for use in conventional manner in admixture with one or more physiologically acceptable carriers or excipients.

Thus, in another aspect of the invention, there is provided a pharmaceutical composition comprising a compound of the invention or a pharmaceutically acceptable derivative thereof adapted for use in human or veterinary medicine.

While it is possible for the compounds of the invention or a pharmaceutically acceptable derivative thereof to be administered as the raw chemical, it is preferable to present it as a pharmaceutical formulation. The formulations of the present invention comprise the compounds of the invention or a pharmaceutically acceptable derivative thereof together with one or more acceptable carriers or diluents therefor and optionally other therapeutic ingredients. The carrier(s) must be "acceptable" in the sense of being compatible with the other ingredients of the formulation and not deleterious to the recipient thereof.

The formulations include those suitable for oral, parenteral (including subcutaneous e.g. by injection or by depot tablet, intradermal, intrathecal, intramuscular e.g. by depot and intravenous), rectal and topical (including dermal, buccal and sublingual) administration although the most suitable route may depend upon for example the condition and disorder of the recipient. The formulations may conveniently be presented in unit dosage form and may be prepared by any of the methods well known in the art of pharmacy. All methods include the step of bringing into association the compound of the invention or a pharmaceutically acceptable acid addition salt thereof ("active ingredient") with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets (e.g. chewable tablets in particular for paediatric administration) each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of a sterile liquid carrier, for example, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter, hard fat or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

The compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

In addition to the ingredients particularly mentioned above, the formulations may include other agents conventional in the art having regard to the type of formulation in question, for example those suitable for oral administration may include flavouring agents.

The $EP_4$ receptor compounds for use in the present invention may be used in combination with other therapeutic agents, for example COX-2 inhibitors, such as celecoxib, rofecoxib, valdecoxib or parecoxib; 5-lipoxygenase inhibitors; analgesics such as paracetamol; NSAID's, such as diclofenac, indomethacin, nabumetone, naproxen or ibuprofen; leukotriene receptor antagonists; DMARD's such as methotrexate; sodium channel blockers, such as lamotrigine; N-type calcium channel antagonists; NMDA receptor modulators, such as glycine receptor antagonists; gabapentin, pregabalin and related compounds; tricyclic antidepressants such as amitriptyline; neurone stabilising antiepileptic drugs; mono-aminergic uptake inhibitors such as venlafaxine; opioid analgesics; local anaesthetics; $5HT_1$ agonists, such as triptans, for example sumatriptan, naratriptan, zolmitriptan, eletriptan, frovatriptan, almotriptan or rizatriptan; $EP_1$ receptor ligands; $EP_2$ receptor ligands; $EP_3$ receptor ligands; $EP_1$ antagonists; $EP_2$ antagonists and $EP_3$ antagonists; cannabanoid receptor agonists; VR1 antagonists. When the compounds are used in combination with other therapeutic agents, the compounds may be administered either sequentially or simultaneously by any convenient route.

The invention thus provides, in a further embodiment, a combination comprising a compound of the invention or a pharmaceutically acceptable derivative thereof together with a further therapeutic agent or agents.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

When a compound of the invention or a pharmaceutically acceptable derivative thereof is used in combination with a second therapeutic agent active against the same disease, the dose of each compound may differ from that when the compound is used alone. Appropriate doses will be readily appreciated by those skilled in the art.

A proposed daily dosage of a compound of the invention, or a pharmaceutically acceptable salt thereof, for the treatment of man is from 0.001 to 30 mg/kg body weight per day and more particularly 0.1 to 3 mg/kg body weight per day, calculated as the free acid, which may be administered as a single or divided dose, for example one to four times per day. The dose range for adult human beings is generally from 0.1 to 1000 mg/day, such as from 10 to 800 mg/day, preferably 10 to 200 mg/day, calculated as the free acid.

The precise amount of the compounds of the invention administered to a host, particularly a human patient, will be the responsibility of the attendant physician. However, the dose employed will depend on a number of factors including the age and sex of the patient, the precise condition being treated and its severity, the route of administration, and any possible combination therapy that may be being undertaken.

The compounds of the invention may be prepared according to Schemes 1, 2 and 3 below in which they are denoted generally as "Formula (I)".

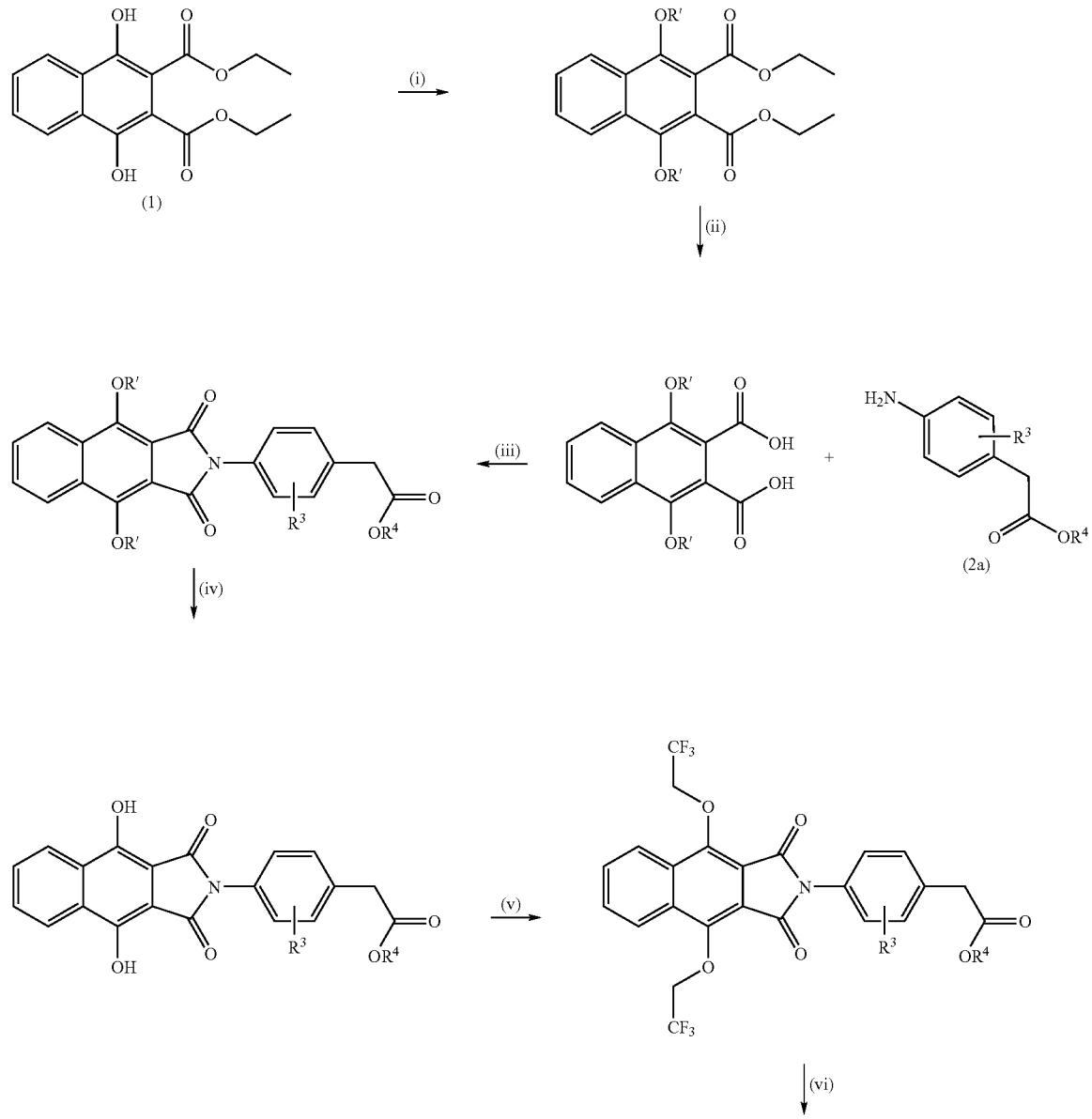

-continued
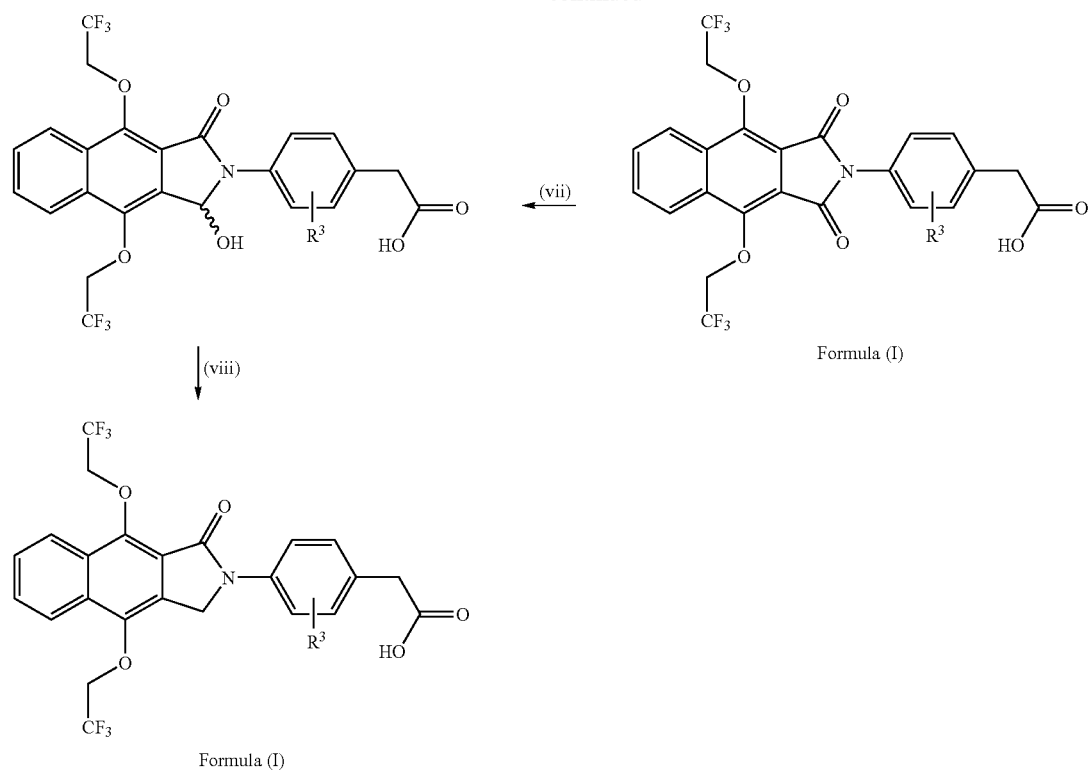
Formula (I)
(i) R'—Br, $K_2CO_3$, $(CH_3)_2CO$; (ii) NaOH, EtOH; (iii) DMAP, $CH_3CO_2H$; (iv) $BBr_3$, DCM;
(v) DMF, $Na_2CO_3$, 2,2,2-trifluoroethyl trifluoromethanesulfonate; (vi) $CH_3CO_2H$, 2N HCl (1:1);
(vii) $NaBH_4$, THF; (viii) TFA, $Et_3SiH$; (wherein R' and R" represent a suitable protecting group
such as —$CH_2Ph$; $R^3$ represents chloro; and $R^4$ represents $C_{1-6}$ alkyl).
Scheme 2
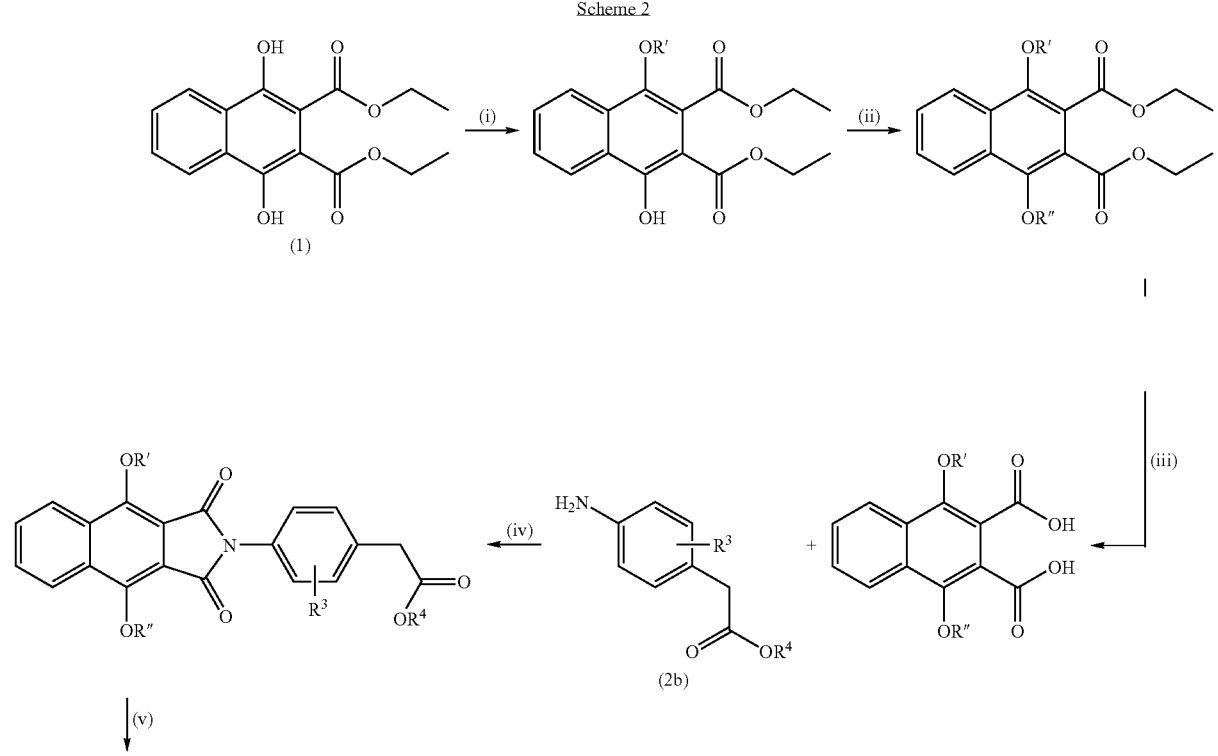

13

14

-continued

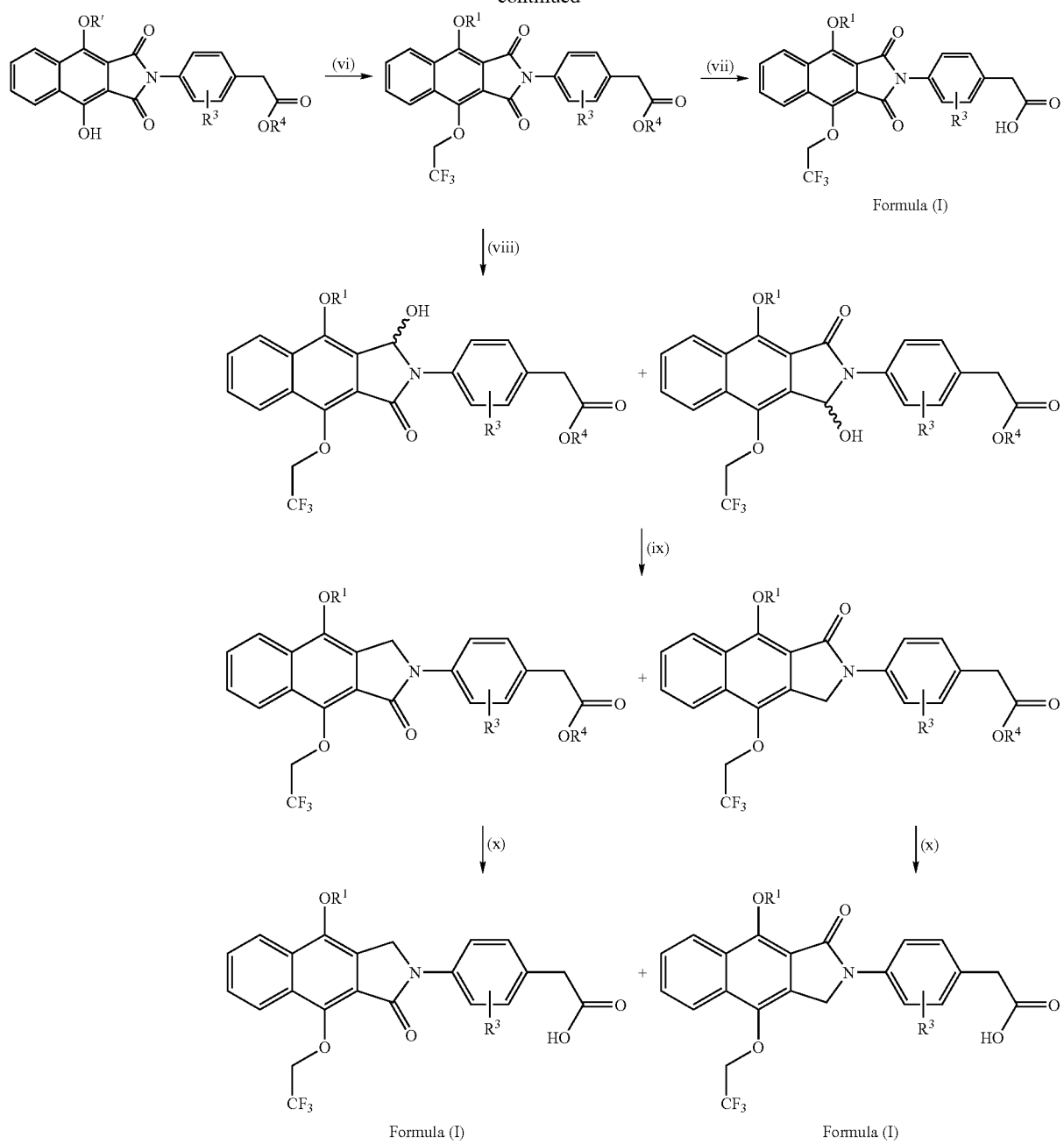

(i) R'—Br, K₂CO₃, (CH₃)₂CO; (ii) R"—Br, K₂CO₃, (CH₃)₂CO; (iii) EtOH, 2N NaOH; (iv) DMAP, CH₃CO₂H; (v) Pd/C, H₂; (vi) DMF, Na₂CO₃, 2,2,2-trifluoroethyl trifluoromethanesulfonate; (vii) CH₃CO₂H, 2N HCl (1:1); (viii) NaBH₄, THF/EtOH; (ix) TFA, Et₃SiH; (x) 2N HCl, CH₃CO₂H (wherein R' and R" represent a suitable protecting group, such as —CH₂Ph, or a C₁₋₄ alkyl group; R³ represents fluoro; and R⁴ represents C₁₋₆ alkyl).

Scheme 3

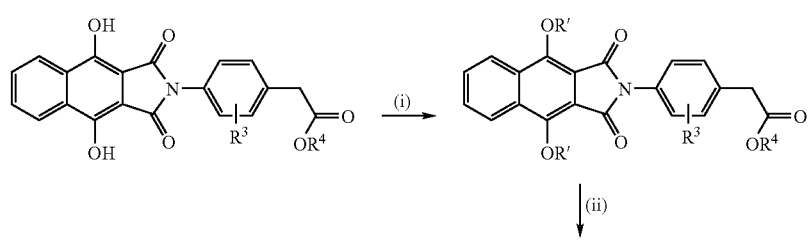

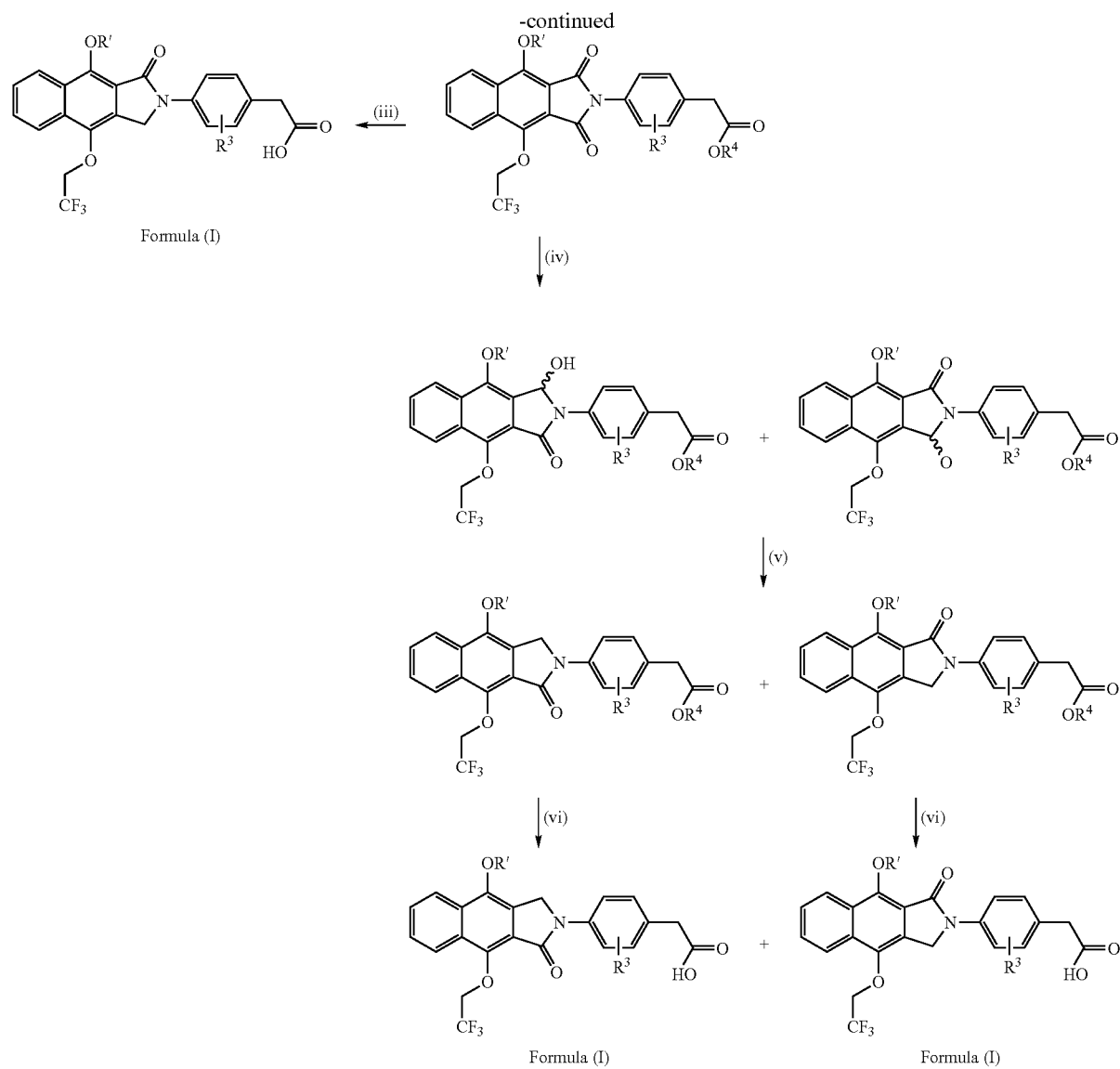
(i) EtI, K$_2$CO$_3$, (CH$_3$)$_2$CO; (ii) DMF, Na$_2$CO$_3$, 2,2,2-trifluoroethyl trifluoromethanesulfonate;
(iii) CH$_3$CO$_2$H, 2N HCl (1:1); (iv) NaBH$_4$, THF/EtOH; (v) TFA, Et$_3$SiH; (vi) 2N NaOH:EtOH
(1:1) (where R' represents C$_{1-4}$ alkyl; R$^3$ represents Cl; and R$^4$ represents C$_{1-6}$ alkyl).
Compounds of formula (2a) may be prepared according to Scheme 4 below:
Compounds of formula (2b) may be prepared according to Scheme 5 below:
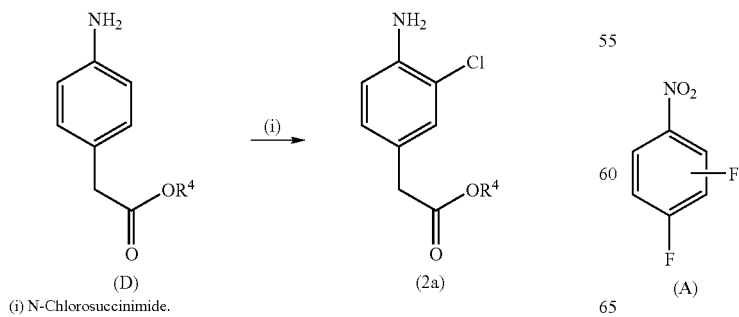
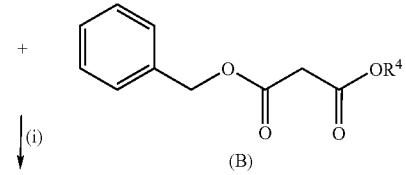

-continued

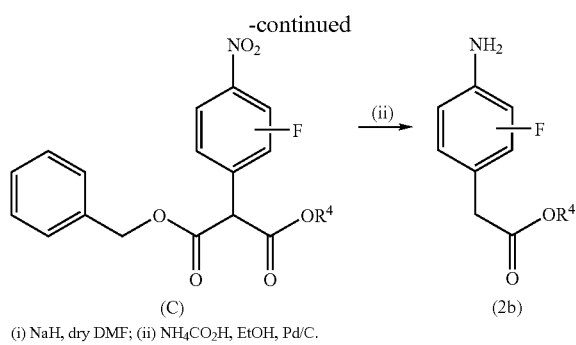

(i) NaH, dry DMF; (ii) NH₄CO₂H, EtOH, Pd/C.

Compound (1) may be prepared in accordance with the method disclosed in International Patent Application, Publication Number WO 02/064564.

Compounds of formula (A) are commercially available or may be prepared in accordance with methods known in the art (for example, 3,4-difluoronitrobenzene may be purchased from Sigma-Aldrich Co. Ltd.).

Compounds of formula (B) are commercially available or may be prepared in accordance with methods known in the art (for example, benzyl ethyl malonate may be purchased from Sigma-Aldrich Co. Ltd.).

Compounds of formula (D) are commercially available or may be prepared in accordance with methods known in the art (for example, ethyl 4-aminophenyl acetate may be purchased from Avocado Research).

The following Descriptions and Examples illustrate the preparation of the compounds of the invention. Descriptions refer to intermediate compounds.

Abbreviations
DCM Dichloromethane
DMAP 4-(Dimethylamino)pyridine
DMF Dimethylformamide
EtOH Ethanol
2N HCl 2 Normal Hydrochloric Acid
LC/MS Liquid chromatography/Mass spectroscopy
MDAP Mass Directed Auto Preparation
MeOH Methanol
NaOH Sodium hydroxide
TFA Trifluoroacetic acid
THF Tetrahydrofuran Analytical Procedures

LC/MS

Column:
Waters Atlantis (4.6 mm×50 mm). Stationary phase particle size, 3 μm.

Solvents:
A: Aqueous solvent=Water+0.05% Formic Acid
B: Organic solvent=Acetonitrile+0.05% Formic Acid Method:

| Time/min | % B |
|---|---|
| 0 | 3 |
| 0.1 | 3 |
| 4 | 97 |
| 4.8 | 97 |
| 4.9 | 3 |
| 5.0 | 3 |

Flow rate, 3 ml/mins.
Injection volume, 5 μl.

Column temperature, 30° C.
UV detection range, 220 to 330 nm.
All retention times are measured in minutes.

Purification Techniques

Purification of the Examples may be carried out by conventional methods such as chromatography and/or recrystallisation using suitable solvents. Chromatographic methods include column chromatography, flash chromatography, HPLC (high performance liquid chromatography), SFC (supercritical fluid chromatography), and MDAP (mass directed autopreparation). The term "Biotage" when used herein refers to commercially available pre-packed silica gel cartridges.

Mass Directed Auto Preparation (MDAP)

Column:
Waters Atlantis: 19 mm×100 mm (small scale); and 30 mm×100 mm (large scale).

Stationary phase particle size, 5 μm.

Solvents:
A: Aqueous solvent=Water+0.1% Formic Acid
B: Organic solvent=Acetonitrile+0.1% Formic Acid
Make up solvent=Methanol:Water 80:20
Needle rinse solvent=Methanol Methods:
Methods were used depending on the analytical retention time of the compound of interest:

(1) Large/Small Scale 1.0-1.5=5-30% B
(2) Large/Small Scale 1.5-2.2=15-55% B
(3) Large/Small Scale 2.2-2.9=30-85% B
(4) Large/Small Scale 2.9-3.6=50-99% B
(5) Large/Small Scale 3.6-5.0=80-99% B
MDP (shallow gradient) 1.5-1.9=13-29% B
MDP (shallow gradient) 1.9-2.3=25-41% B
MDP (shallow gradient) 2.3-2.6=37-53% B
MDP (shallow gradient) 2.6-3.1=49-65% B
MDP (shallow gradient) 3.1-3.6=61-77% B
MDP (shallow gradient) 3.6-4.0=73-99% B Runtime, 13.5 minutes, comprising 10-minute gradient followed by a 3.5 minute column flush and re-equilibration step.

Flow Rate:
20 mls/min (Small Scale) or 40 mls/min (Large Scale).

Description 1

Diethyl 1,4-bis[(phenylmethyl)oxy]-2,3-naphthalenedicarboxylate

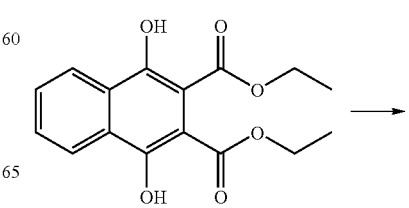

-continued

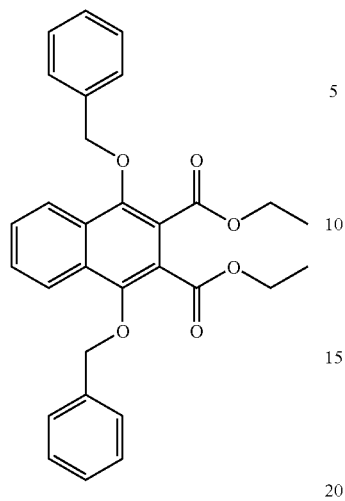

Benzylbromide (2.95 ml, 24.7 mmol) was added to a stirred solution of diethyl 1,4-dihydroxy-2,3-naphthalenedicarboxylate (3 g, 9.87 mmol) and potassium carbonate (3.40 g, 24.7 mmol) in acetone (100 ml). The reaction mixture was refluxed for 18 hours under an atmosphere of argon. The resulting mixture was evaporated and the reaction mixture triturated with water. The resulting tan coloured solid was collected by filtration and washed with water then dried under vacuum to give the title compound (5.23 g, 10.8 mmol). LC/MS: Rt=4.13, [MH]+ 485.

Description 2

1,4-bis[(phenylmethyl)oxy]-2,3-naphthalenedicarboxylic acid

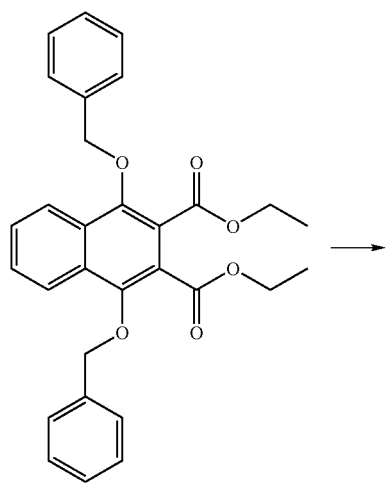

-continued

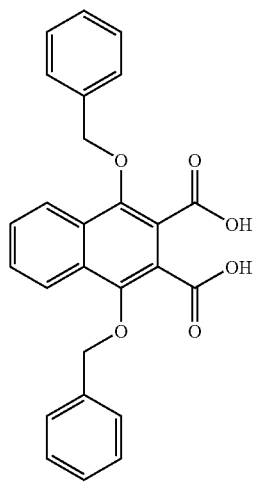

A mixture of diethyl 1,4-bis[(phenylmethyl)oxy]-2,3-naphthalenedicarboxylate (4.78 g, 9.88 mmol), ethanol (75 ml), and 2N aqueous sodium hydroxide solution (75 ml) was refluxed for 2 hours. The reaction mixture was cooled and evaporated. This was acidified with HCl (2N) and the resulting cream solid was collected by filtration and washed with water. This was dried under vacuum to give the title compound (3.79 g, 8.86 mmol). LC/MS: Rt=3.15, [MH]− 427.

Description 3

Ethyl (4-amino-3-chlorophenyl)acetate

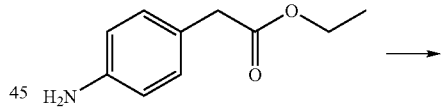

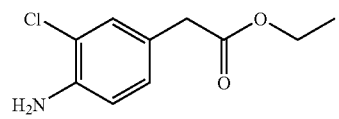

Ethyl-4-aminophenylacetate (20 g, 112 mmol) was dissolved in chloroform (300 ml) and treated with N-chlorosuccinimde (14.92 g, 112 mmol) and stirred for 15 minutes at room temperature under argon. Reaction mixture was washed with water, brine and dried over magnesium sulphate. Evaporated to a brown oil which was purified by chromatography on silica gel eluting with ethyl acetate (0-45%) in hexane to give the title compound as a orange oil (10.12 g, 47.4 mmol). LC/MS: Rt=2.59, [MH]+ 214.

Description 4

Ethyl (3-chloro-4-{1,3-dioxo-4,9-bis[(phenylmethyl)oxy]-1,3-dihydro-2H-benzo[f]isoindol-2-yl}phenyl)acetate

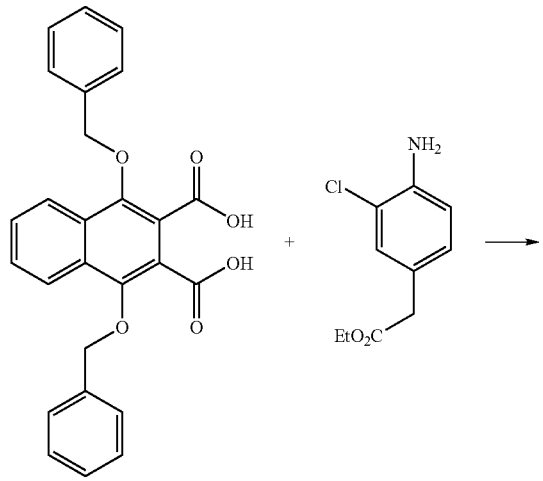

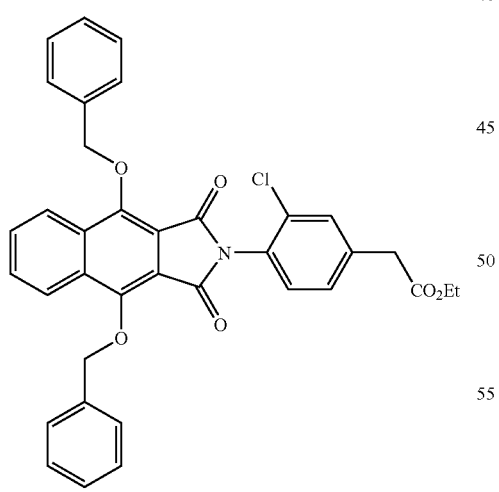

A mixture of 1 1,4-bis[(phenylmethyl)oxy]-2,3-naphthalenedicarboxylic acid (5.0 g, 11.68 mmol), ethyl (4-amino-3-chlorophenyl)acetate (4.74 g, 22.2 mmol) and DMAP (0.427 g, 3.59 mmol) were heated to 120° C. in acetic acid (20 ml) for 18 hours. Water was added and the mixture and resulting brown solid collected by filtration and washed with water. This was triturated with ether to give a cream solid which was collected by filtration and dried in the vacuum oven (5.34 g, 8.83 mmol). LC/MS: Rt=4.15, [MH]+ 606.

Description 5

Ethyl[3-chloro-4-(4,9-dihydroxy-1,3-dioxo-1,3-dihydro-2H-benzo[f]isoindol-2-yl)phenyl]acetate

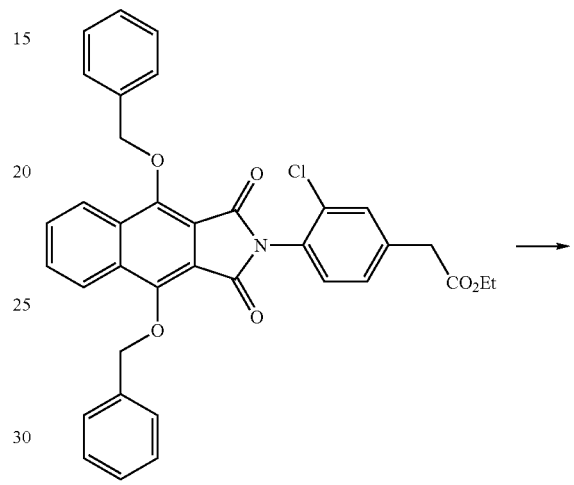

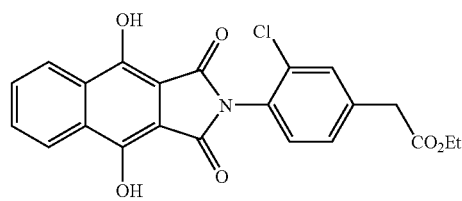

To a solution of ethyl (3-chloro-4-{1,3-dioxo-4,9-bis[(phenylmethyl)oxy]-1,3-dihydro-2H-benzo[f]isoindol-2-yl}phenyl)acetate (0.505 g, 0.84 mmol) in DCM (30 ml), cooled to −78° C. under an atmosphere of argon, was added boron tribromide (0.24 ml, 2.50 mmol) drop wise. Stirred at −78° C. for 25 minutes. The reaction mixture was quenched with water and warmed to room temperature. This was extracted X2 with DCM using a hydrophobic frit. The organic phase was evaporated to an orange solid. Hot trituration in DCM resulted in a yellow solid which was collected by filtration (0.189 g, 0.44 mmol, 53%). The filtrate was purified by chromatography on silica gel, eluting with ethyl acetate (0-70%) in hexane to give the title compound as a yellow solid (0.035 g, 0.082 mmol). LC/MS: Rt=3.22, [MH]+ 426.

Description 6

Ethyl (3-chloro-4-{1,3-dioxo-4,9-bis[(2,2,2-trifluoroethyl)oxy]-1,3-dihydro-2H-benzo[f]isoindol-2-yl}phenyl)acetate

Example 1

(3-Chloro-4-{1,3-dioxo-4,9-bis[(2,2,2-trifluoroethyl)oxy]-1,3-dihydro-2H-benzo[f]isoindol-2-yl}phenyl)acetic acid

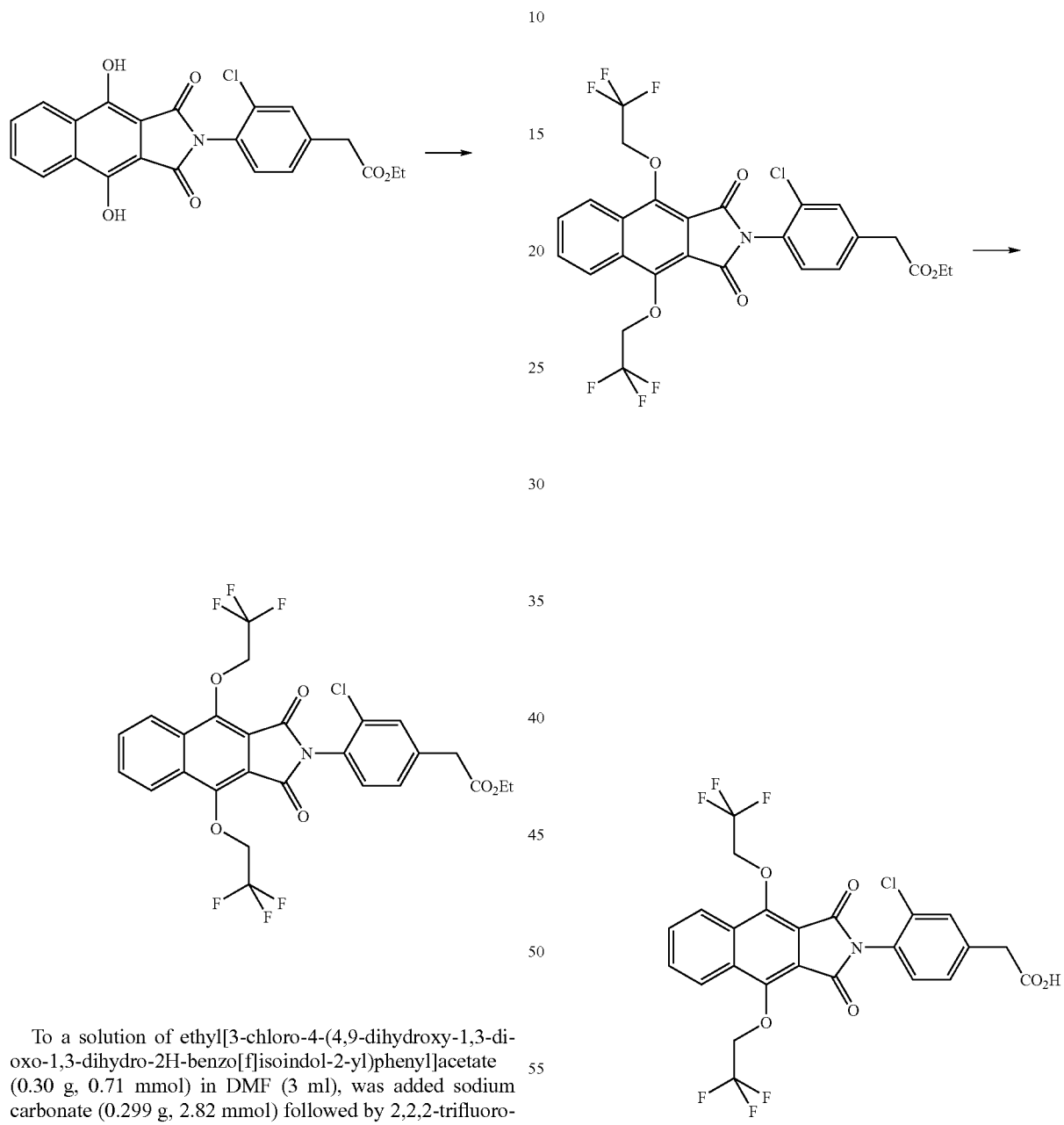

To a solution of ethyl[3-chloro-4-(4,9-dihydroxy-1,3-dioxo-1,3-dihydro-2H-benzo[f]isoindol-2-yl)phenyl]acetate (0.30 g, 0.71 mmol) in DMF (3 ml), was added sodium carbonate (0.299 g, 2.82 mmol) followed by 2,2,2-trifluoroethyl trifluoromethanesulfonate (0.490 g, 2.12 mmol). This was stirred at room temperature for 21 hours. Further sodium carbonate (0.11 g, 1.06 mmol) and 2,2,2-trifluoroethyl trifluoromethanesulfonate (0.246 g, 1.06 mmol) was added to the reaction to drive it to completion. This was then heated to 50° C. for 2.5 hours. Water was added to the reaction mixture with rapid stirring. The resulting tan coloured solid was collected by filtration, washed with water and dried in the vacuum oven to give the title compound (0.377 g, 0.64 mmol). LC/MS: Rt=3.98, [MH]+ 590.

Ethyl (3-chloro-4-{1,3-dioxo-4,9-bis[(2,2,2-trifluoroethyl)oxy]-1,3-dihydro-2H-benzo[f]isoindol-2-yl}phenyl)acetate (0.375 g, 0.64 mmol) was heated to 100° C. in a 1:1 mixture of acetic acid:2N aqueous hydrochloric acid (20 ml) for 5 hours. The reaction was cooled to room temperature. On addition of water, the resulting white solid was collected by filtration and washed with water (0.315 g, 0.56 mmol). LC/MS: Rt=3.57, [MH]+ 562.

Description 7

(3-Chloro-4-{1-hydroxy-3-oxo-4,9-bis[(2,2,2-trifluoroethyl)oxy]-1,3-dihydro-2H-benzo[f]isoindol-2-yl}phenyl)acetic acid

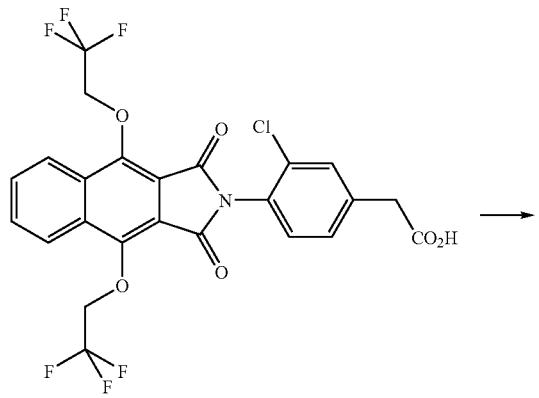

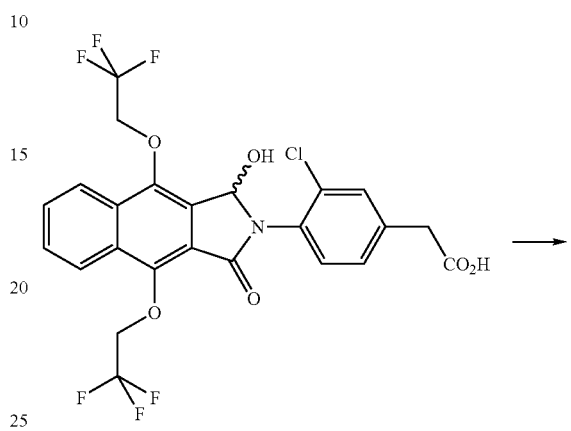

To a solution of (3-chloro-4-{1,3-dioxo-4,9-bis[(2,2,2-trifluoroethyl)oxy]-1,3-dihydro-2H-benzo[f]isoindol-2-yl}phenyl)acetic acid (0.250 g, 0.45 mmol) in ethanol (10 ml) and tetrahydrofuran (20 ml), was added sodium borohydride (0.059 g, 1.56 mmol) in portions. A further addition of sodium borohydride (0.059 g, 1.56 mmol) was made and stirring continued for 10 minutes. The mixture was evaporated and then quenched with aqueous saturated ammonium chloride solution until the mixture was pH 7. This was extracted ×2 with ethyl acetate, washed with brine, dried over magnesium sulphate and evaporated to give the crude product (0.235 g, 0.42 mmol). LC/MS: Rt=3.28, [MH]$^+$564.

Example 2

(3-chloro-4-{1-oxo-4,9-bis[(2,2,2-trifluoroethyl)oxy]-1,3-dihydro-2H-benzo[f]isoindol-2-yl}phenyl) acetic acid

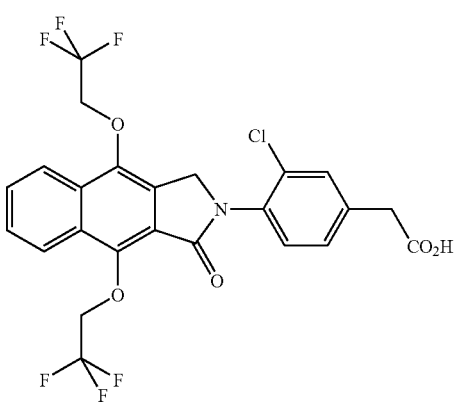

To a solution of (3-chloro-4-{1-hydroxy-3-oxo-4,9-bis[(2,2,2-trifluoroethyl)oxy]-1,3-dihydro-2H-benzo[f]isoindol-2-yl}phenyl)acetic acid (0.235 g, 0.42 mmol) in trifluoroacetic acid (5 ml) cooled to 0° C., was added triethylsilane (0.10 ml, 0.63 mmol). Stirring continued at 0° C. for 5 minutes and then the mixture was evaporated. The crude mixture was purified using MDAP. The clean fractions were evaporated to give a white solid. This was triturated with ether, the resulting white solid collected by filtration (0.008 g, 0.015 mmol). LC/MS: Rt=3.49, [MH]$^+$548.

Description 8

Diethyl 1-(ethyloxy)-4-hydroxy-2,3-naphthalenedicarboxylate

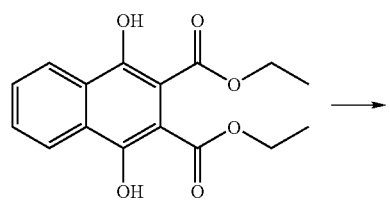

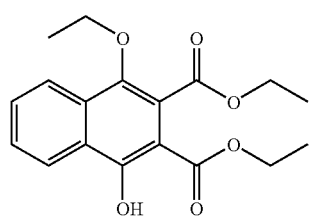

Bromoethane (0.359 g, 3.29 mmol) was added to a stirred solution of diethyl 1,4-dihydroxy-2,3-naphthalenedicarboxylate (1 g, 3.29 mmol) and potassium carbonate (0.454 g, 3.29 mmol) in acetone (25 ml). The reaction mixture was refluxed for 24 hours under an atmosphere of argon. The resulting mixture was evaporated and the residue was partitioned between 2× ethylacetate and water. The combined organics were washed with water and dried over magnesium sulphate. The orange oil was purified by chromatography on silica gel, eluting with ethyl acetate (0-10%) in hexane to give the title compound as a clear oil (0.661 g, 1.99 mmol). LC/MS: Rt=3.63, [MH]⁻ 331.

Description 9

Diethyl 1-(ethyloxy)-4-[(phenylmethyl)oxy]-2,3-naphthalenedicarboxylate

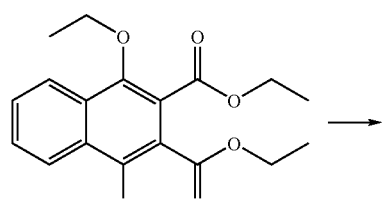

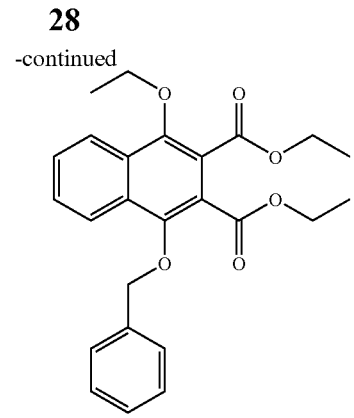

Benzyl bromide (1.32 ml, 11.1 mmol) was added to a stirred solution of diethyl 1-(ethyloxy)-4-hydroxy-2,3-naphthalenedicarboxylate (2.45 g, 7.38 mmol) and potassium carbonate (1.53 g, 11.1 mmol) in acetone (50 ml). The reaction mixture was refluxed for 1 hour under an atmosphere of argon. The resulting mixture was evaporated and the residue was partitioned between 2× ethylacetate and brine. The combined organics were washed with water and dried over magnesium sulphate. The clear oil was purified by chromatography on silica gel, eluting with ethyl acetate (0-40%) in hexane to give the title compound as clear oil (3.05 g, 7.23 mmol). LC/MS: Rt=3.77, [MH]⁺ 423

Description 10

1-(Ethyloxy)-4-[(phenylmethyl)oxy]-2,3-naphthalenedicarboxylic acid

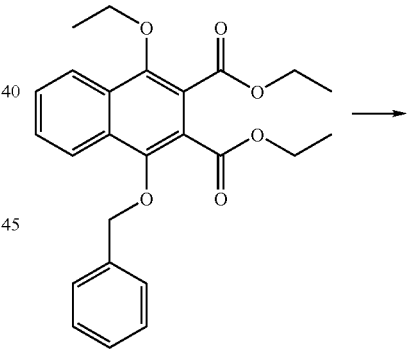

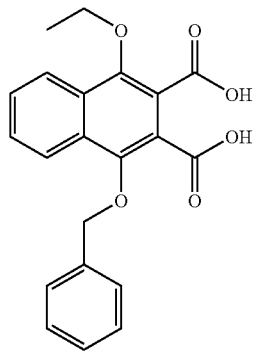

A mixture of diethyl 1-(ethyloxy)-4-[(phenylmethyl)oxy]-2,3-naphthalenedicarboxylate (3.05 g, 7.23 mmol), ethanol (30 ml), and 2N aqueous sodium hydroxide solution (35 ml)

was refluxed for 3 hours. The reaction mixture was cooled and evaporated. This was acidified with HCl (2N) and extracted with 2× ethyl acetate. Combined organics were dried over magnesium sulphate and the solvent evaporated to give the title compound as a white solid (2.55 g, 6.97 mmol). LC/MS: Rt=2.76, [MH]⁻ 365.

ethyl acetate in hexane to give the title compound as a yellow oil (11.66, 32.3 mmol). LC/MS: Rt=3.39, [MH]⁻ 360.

Description 12

Ethyl (4-amino-3-fluorophenyl)acetate

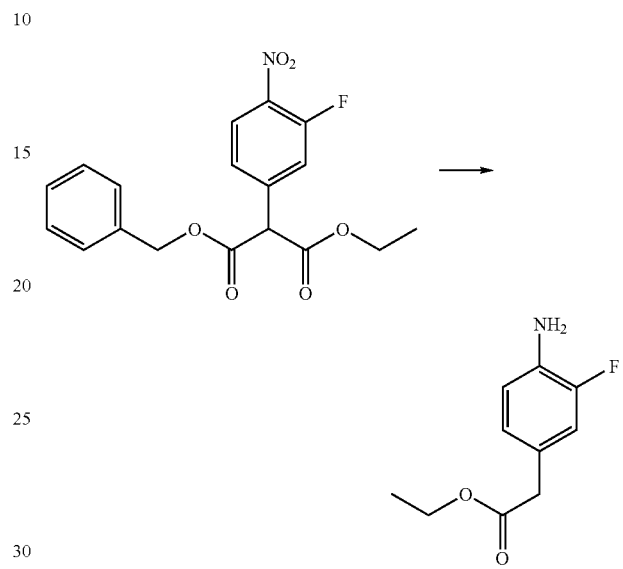

Description 11

Ethyl phenylmethyl (3-fluoro-4-nitrophenyl)propanedioate

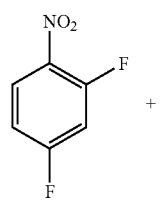

+

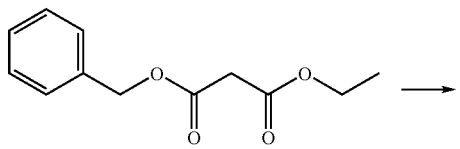

Ethyl phenylmethyl (3-fluoro-4-nitrophenyl)propanedioate (11.66 g, 32.3 mmol), ammonium formate (10.2 g, 161.5 mmol) and 10% palladium on carbon (wet paste) (1.7 g, 0.8 mmol) was placed under argon and ethanol (300 ml) introduced. The reaction mixture was heated to 60° C. for 3 hours, cooled and filtered through celite under an argon atmosphere. Evaporated and purified by chromatography on silica gel eluting with 2-30% ethyl acetate in hexane to give the title compound as a yellow oil (5.22 g, 26.5 mmol). LC/MS: Rt=2.14, [MH]⁺ 198.

Description 13

Ethyl (4-{4-(ethyloxy)-1,3-dioxo-9-[(phenylmethyl)oxy]-1,3-dihydro-2H-benzo[f]isoindol-2-yl}-3-fluorophenyl)acetate

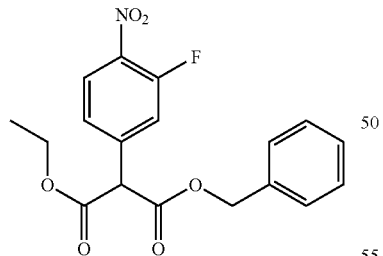

Sodium hydride (17.8 g, 445 mmol) was added portionwise to a solution of benzyl ethyl malonate (98.9, 445 mmol) in dry DMF (280 ml) and stirred for 10 minutes. Cooled to 10° C. over 30 minutes. 2,4-difluoro-1-nitrobenzene (48.9 ml, 445 mmol) was added and stirred at room temperature for 16 hours. The reaction mixture was quenched with 2N hydrochloric acid (150 ml) to pH 3-4 then extracted ×2 with ether. The combined organics washed with 2× water and brine, dried over magnesium sulphate and evaporated to a yellow oil. Purified by chromatography on silica gel eluting with 5%

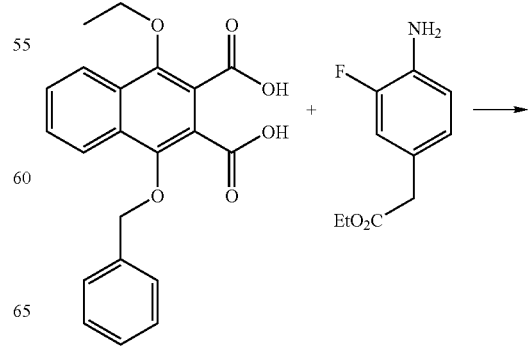

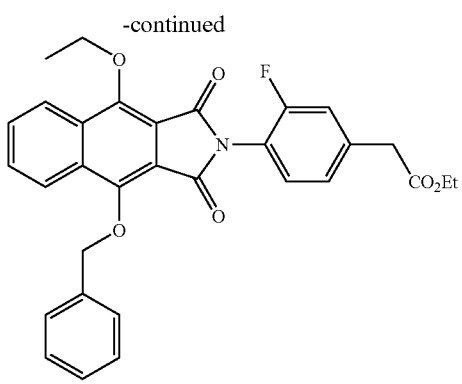

A mixture of 1-(ethyloxy)-4-[(phenylmethyl)oxy]-2,3-naphthalenedicarboxylic acid (1.40 g, 3.32 mmol), ethyl (4-amino-3-fluorophenyl)acetate (1.24 g, 6.30 mmol) and DMAP (0.121 g, 0.995 mmol) were heated to 120° C. in acetic acid (20 ml) for 6 hours. The reaction mixture was triturated with water and the resulting yellow solid was collected by filtration and dried in the vacuum oven to give the title compound (1.93 g, 3.66 mmol). LC/MS: Rt=3.95, [MH]$^+$ 528.

Description 14

Ethyl {4-[4-(ethyloxy)-9-hydroxy-1,3-dioxo-1,3-dihydro-2H-benzo[f]isoindol-2-yl]-3-fluorophenyl}acetate

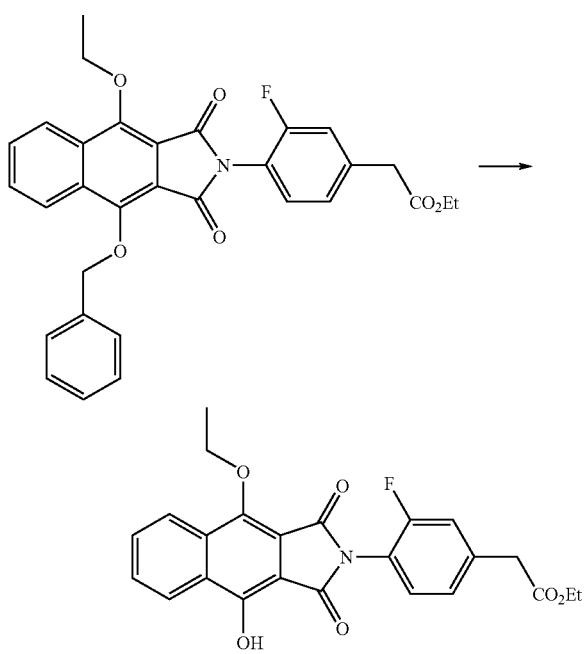

10% Palladium on carbon (0.175 g) was suspended in ethanol (150 ml), to this was added ethyl (4-{4-(ethyloxy)-1,3-dioxo-9-[(phenylmethyl)oxy]-1,3-dihydro-2H-benzo[f]isoindol-2-yl}-3-fluorophenyl)acetate (1.75 g, 3.32 mmol). The reaction was stirred at room temperature under an atmosphere of hydrogen for 3 hours. This was filtered through a bed of celite under a blanket of argon, and washed with dichloromethane. The filtrate was evaporated to give a yellow solid (1.56 g, 3.57 mmol). LC/MS: Rt=3.50, [MH]$^+$ 438.

Description 15

Ethyl (4-{4-(ethyloxy)-1,3-dioxo-9-[(2,2,2-trifluoro-ethyl)oxy]-1,3-dihydro-2H-benzo[f]isoindol-2-yl}-3-fluorophenyl)acetate

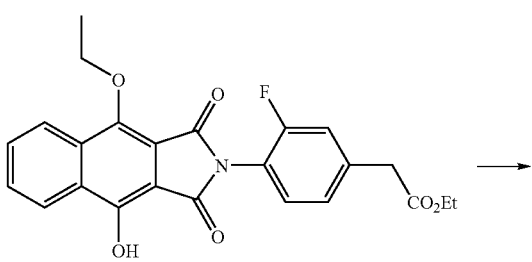

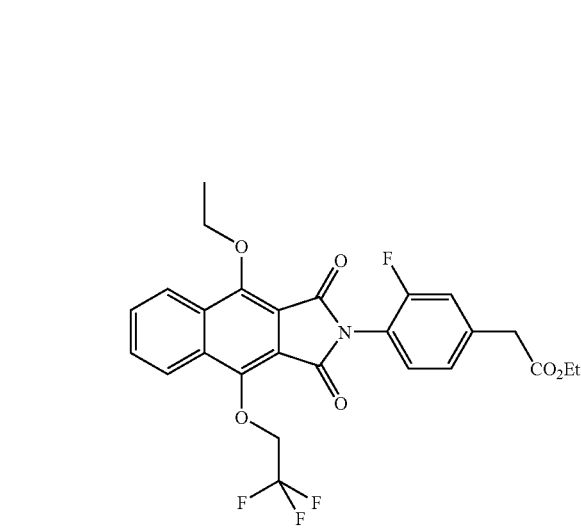

To a solution ethyl {4-[4-(ethyloxy)-9-hydroxy-1,3-dioxo-1,3-dihydro-2H-benzo[f]isoindol-2-yl]-3-fluorophenyl}acetate (0.2 g, 0.458 mmol) in DMF (3 ml), was added sodium carbonate (0.097 g, 0.915 mmol) followed by 2,2,2-trifluoroethyl trifluoromethanesulfonate (0.159 g, 0.687 mmol). This was stirred at room temperature for 24 hours. Water was added to the reaction mixture with rapid stirring. The resulting yellow coloured solid was collected by filtration, washed with water and dried in the vacuum oven to give the title compound (0.119 g, 0.23 mmol). LC/MS: Rt=3.82, [MH]$^+$ 520.

Example 3

(4-{4-(Ethyloxy)-1,3-dioxo-9-[(2,2,2-trifluoroethyl)oxy]-1,3-dihydro-2H-benzo[f]isoindol-2-yl}-3-fluorophenyl)acetic acid

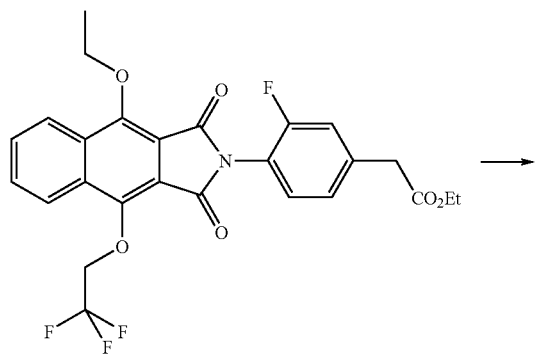

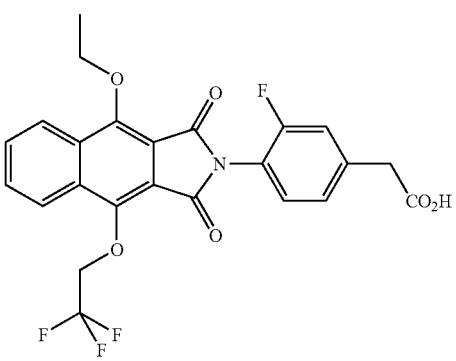

Ethyl (4-{4-(ethyloxy)-1,3-dioxo-9-[(2,2,2-trifluoroethyl)oxy]-1,3-dihydro-2H-benzo[f]isoindol-2-yl}-3-fluorophenyl)acetate (0.119 g, 0.23 mmol) was heated to 100° C. in a 1:1 mixture of acetic acid:2N aqueous hydrochloric acid (10 ml) for 2 hours. On addition of water, the resulting cream solid was collected by filtration and washed with water. This was purified by MDAP to give the title compound as a white solid (0.073 g, 0.15 mmol). LC/MS: Rt=3.38, [MH]$^+$ 492.

Description 16

Ethyl {3-chloro-4-[4-(ethyloxy)-9-hydroxy-1,3-dioxo-1,3-dihydro-2H-benzo[f]isoindol-2-yl]phenyl}acetate

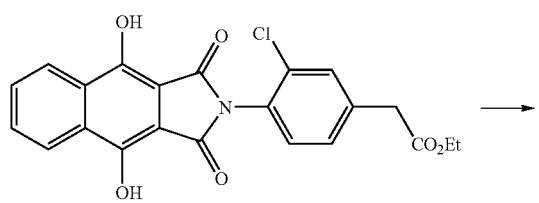

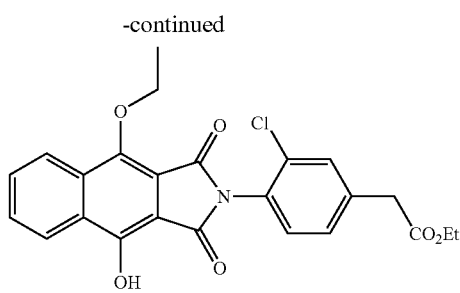

To a solution of ethyl[3-chloro-4-(4,9-dihydroxy-1,3-dioxo-1,3-dihydro-2H-benzo[f]isoindol-2-yl)phenyl]acetate (2.0 g, 4.70 mmol) in acetone (50 ml), was added potassium carbonate (0.656 g, 4.75 mmol) followed by iodoethane (0.38 ml, 4.75 mmol). This was heated at reflux for 24 hours. The solvent was evaporated and water added to the residue. The resulting gummy brown solid was collected by filtration and dried in the vacuum oven. This was purified using reverse phase chromatography to give the title compound (1.21 g, 2.67 mmol). LC/MS: Rt=3.66, [MH]$^+$ 454.

Description 17

Ethyl (3-chloro-4-{4-(ethyloxy)-1,3-dioxo-9-[(2,2,2-trifluoroethyl)oxy]-1,3-dihydro-2H-benzo[f]isoindol-2-yl}phenyl)acetate

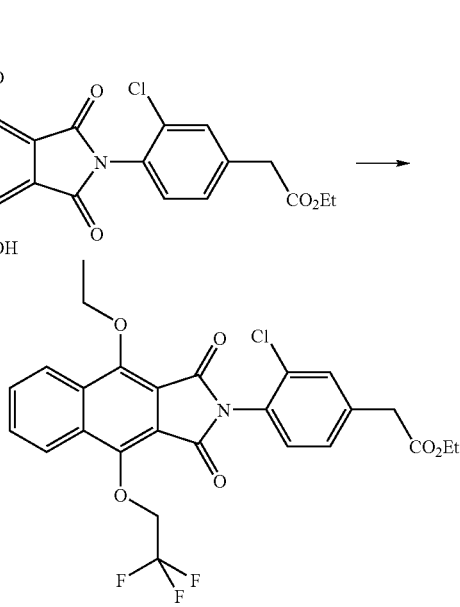

To a solution of ethyl {3-chloro-4-[4-(ethyloxy)-9-hydroxy-1,3-dioxo-1,3-dihydro-2H-benzo[f]isoindol-2-yl]phenyl}acetate (0.60 g, 1.32 mmol) in DMF (6 ml), was added sodium carbonate (0.280 g, 2.65 mmol) followed by 2,2,2-trifluoroethyl trifluoromethanesulfonate (0.460 g, 1.98 mmol). This was stirred at room temperature for 5 hours. Water was added to the reaction mixture and the resulting brown solid was collected by filtration. This was purified by chromatography on silica gel eluting with 5-60% ethylacetate in hexane to give the title compound (0.258 g, 0.48 mmol). LC/MS: Rt=3.85, [MH]+ 536.

Example 4

(3-Chloro-4-{4-(ethyloxy)-1,3-dioxo-9-[(2,2,2-trifluoroethyl)oxy]-1,3-dihydro-2H-benzo[f]isoindol-2-yl}phenyl)acetic acid

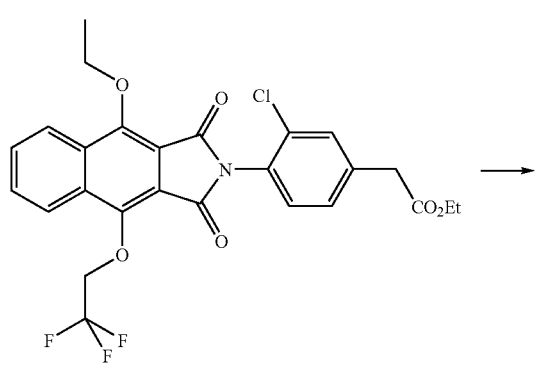

Ethyl (3-chloro-4-{4-(ethyloxy)-1,3-dioxo-9-[(2,2,2-trifluoroethyl)oxy]-1,3-dihydro-2H-benzo[f]isoindol-2-yl}phenyl)acetate (0.060 g, 0.11 mmol) was heated to 100° C. in a 1:1 mixture of acetic acid:HCl (2N) (6 ml) for 1.25 hours. On addition of water, the resulting white solid was collected by filtration and washed with water (0.047 g, 0.09 mmol). LC/MS: Rt=3.44, [MH]+ 508.

Description 18

Ethyl (3-chloro-4-{4-(ethyloxy)-1-hydroxy-3-oxo-9-[(2,2,2-trifluoroethyl)oxy]-1,3-dihydro-2H-benzo[f]isoindol-2-yl}phenyl)acetate-Ethyl (3-chloro-4-{4-(ethyloxy)-3-hydroxy-1-oxo-9-[(2,2,2-trifluoroethyl)oxy]-1,3-dihydro-2H-benzo[f]isoindol-2-yl}phenyl)acetate To a solution of ethyl (3-chloro-4-{4-(ethyloxy)-1,3-dioxo-9-[(2,2,2-trifluoroethyl)oxy]-1,3-dihydro-2H-benzo[f]isoindol-2-yl}phenyl)acetate (0.200 g, 0.37 mmol) in ethanol (10 ml) and tetrahydrofuran (20 ml), was added sodium borohydride (0.043 g, 1.12 mmol) in portions. Total further additions of sodium borohydride (1.45 g, 38.1 mmol) and tetrahydrofuran were made over 4 hours to drive the reaction to completion. The mixture was evaporated and then quenched with aqueous saturated ammonium chloride solution until the mixture was pH 7. This was extracted ×2 with ethyl acetate, washed with brine, dried over magnesium sulphate and evaporated to give the crude product (0.163 g, 0.30 mmol). LC/MS: Rt=3.42, 3.47, [MH]$^+$538.

The following compounds were prepared in a similar manner to ethyl (3-chloro-4-{4-(ethyloxy)-1-hydroxy-3-oxo-9-[(2,2,2-trifluoroethyl)oxy]-1,3-dihydro-2H-benzo[f]isoindol-2-yl}phenyl)acetate-ethyl (3-chloro-4-{4-(ethyloxy)-3-hydroxy-1-oxo-9-[(2,2,2-trifluoroethyl)oxy]-1,3-dihydro-2H-benzo[f]isoindol-2-yl}phenyl)acetate using the appropriate starting material.

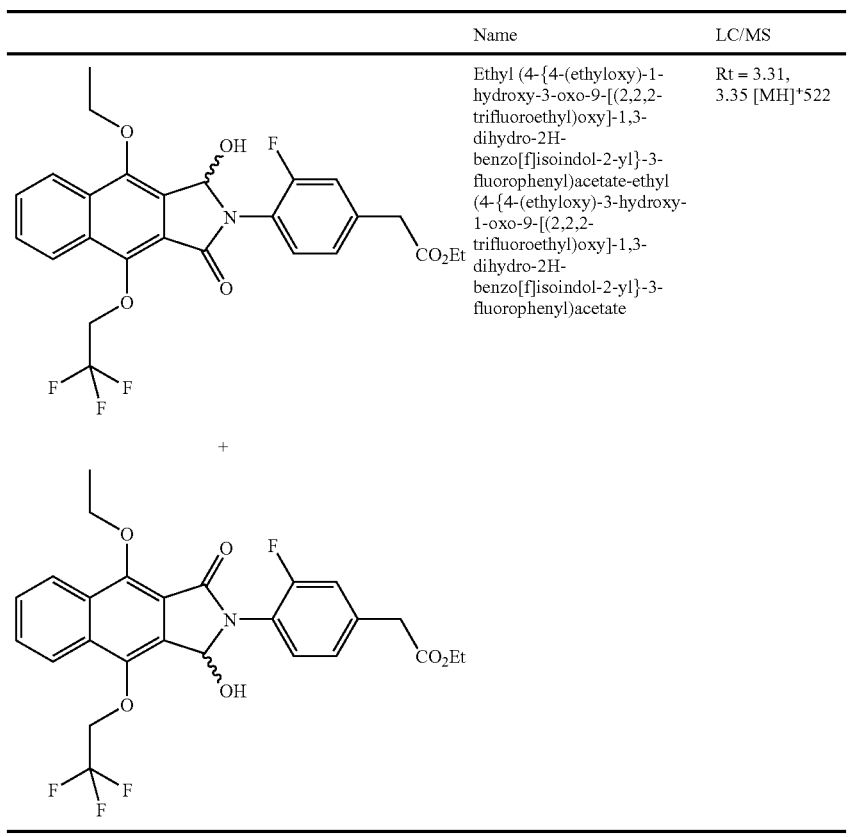

| | Name | LC/MS |
|---|---|---|
| | Ethyl (4-{4-(ethyloxy)-1-hydroxy-3-oxo-9-[(2,2,2-trifluoroethyl)oxy]-1,3-dihydro-2H-benzo[f]isoindol-2-yl}-3-fluorophenyl)acetate-ethyl (4-{4-(ethyloxy)-3-hydroxy-1-oxo-9-[(2,2,2-trifluoroethyl)oxy]-1,3-dihydro-2H-benzo[f]isoindol-2-yl}-3-fluorophenyl)acetate | Rt = 3.31, 3.35 [MH]$^+$522 |

Description 19

Ethyl (3-chloro-4-{9-(ethyloxy)-1-oxo-4-[(2,2,2-trifluoroethyl)oxy]-1,3-dihydro-2H-benzo[f]isoindol-2-yl}phenyl)acetate-Ethyl (3-chloro-4-{4-(ethyloxy)-1-oxo-9-[(2,2,2-trifluoroethyl)oxy]-1,3-dihydro-2H-benzo[f]isoindol-2-yl}phenyl)acetate

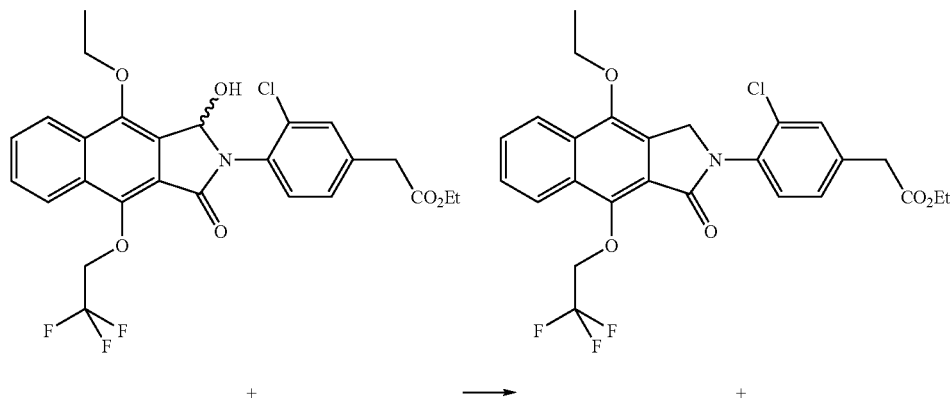

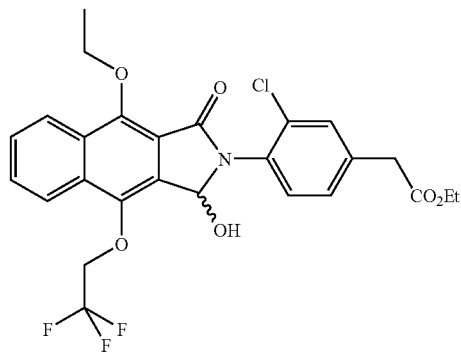

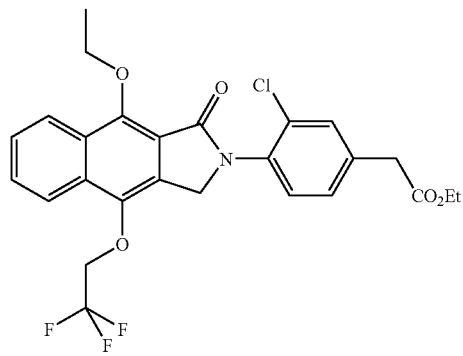

To a solution of ethyl (3-chloro-4-{4-(ethyloxy)-1-hydroxy-3-oxo-9-[(2,2,2-trifluoroethyl)oxy]-1,3-dihydro-2H-benzo[f]isoindol-2-yl}phenyl)acetate-ethyl (3-chloro-4-{4-(ethyloxy)-3-hydroxy-1-oxo-9-[(2,2,2-trifluoroethyl)oxy]-1,3-dihydro-2H-benzo[f]isoindol-2-yl}phenyl)acetate (0.163 g, 0.30 mmol) in trifluoroacetic acid (5 ml) cooled to 0° C., was added triethylsilane (0.07 ml, 0.45 mmol). Stirring continued at 0° C. for 10 minutes and then the mixture was evaporated. The isomers were separated using MDAP (shallow gradient)

Ethyl (3-chloro-4-{9-(ethyloxy)-1-oxo-4-[(2,2,2-trifluoroethyl)oxy]-1,3-dihydro-2H-benzo[f]isoindol-2-yl}phenyl)acetate Ethyl (3-chloro-4-{4-(ethyloxy)-1-oxo-9-[(2,2,2-trifluoroethyl)oxy]-1,3-dihydro-2H-benzo[f]isoindol-2-yl}phenyl)acetate

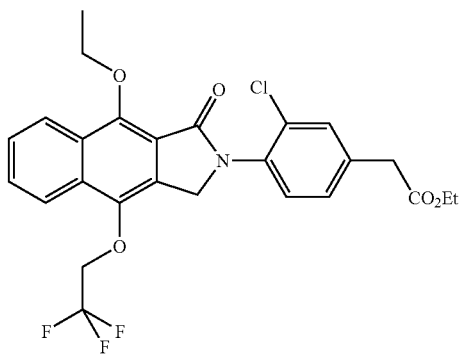

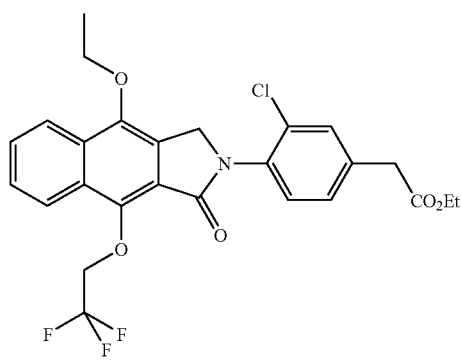

(0.041 g, 0.08 mmol). LC/MS: Rt=3.87, [MH]$^+$522.

(0.054 g, 0.10 mmol). LC/MS: Rt=3.76, [MH]$^+$522.

The following compounds were prepared in a similar manner to ethyl (3-chloro-4-{9-(ethyloxy)-1-oxo-4-[(2,2,2-trifluoroethyl)oxy]-1,3-dihydro-2H-benzo[f]isoindol-2-yl}phenyl)acetate-ethyl (3-chloro-4-{4-(ethyloxy)-1-oxo-9-[(2,2,2-trifluoroethyl)oxy]-1,3-dihydro-2H-benzo[f]isoindol-2-yl}phenyl)acetate using the appropriate starting material.

| Name | LC/MS |
|---|---|
| Ethyl (4-{9-(ethyloxy)-1-oxo-4-[(2,2,2-trifluoroethyl)oxy]-1,3-dihydro-2H-benzo[f]isoindol-2-yl}-3-fluorophenyl)acetate | Rt = 3.71 [MH]⁺506 |
| Ethyl (4-{4-(ethyloxy)-1-oxo-9-[(2,2,2-trifluoroethyl)oxy]-1,3-dihydro-2H-benzo[f]isoindol-2-yl}-3-fluorophenyl)acetate | Rt = 3.81 [MH]⁺506 |

Example 5

(3-Chloro-4-{4-(ethyloxy)-1-oxo-9-[(2,2,2-trifluoroethyl)oxy]-1,3-dihydro-2H-benzo[f]isoindol-2-yl}phenyl)acetic acid

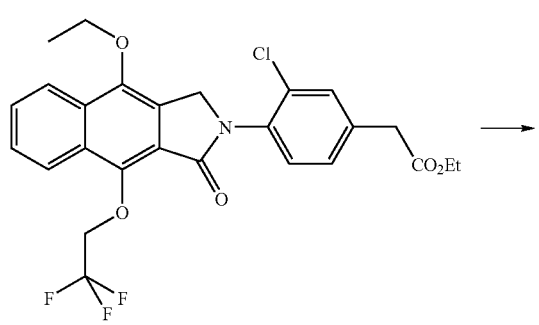

⟶

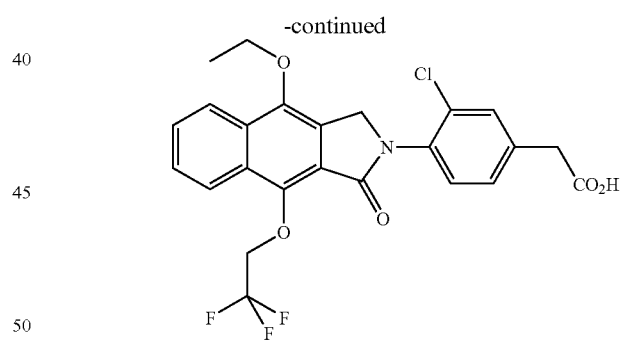

Ethyl (3-chloro-4-{4-(ethyloxy)-1-oxo-9-[(2,2,2-trifluoroethyl)oxy]-1,3-dihydro-2H-benzo[f]isoindol-2-yl}phenyl)acetate (0.041 g, 0.08 mmol) was heated to reflux in a 1:1 mixture of 2N sodium hydroxide:ethanol (10 ml) for 1 hour. The reaction was cooled to room temperature. The ethanol was evaporated and the mixture acidified with HCl (2N). The resulting white solid was collected by filtration, washed with water and dried under vacuum. This was purified by MDAP to give the title compound (0.014 g, 0.03 mmol) as a clear foam. LC/MS: Rt=3.42, [MH]⁺ 494.

The following compound was prepared in a similar manner to (3-Chloro-4-{4-(ethyloxy)-1-oxo-9-[(2,2,2-trifluoroethyl)oxy]-1,3-dihydro-2H-benzo[f]isoindol-2-yl}phenyl)acetic acid using the appropriate starting material.

| | | Name | LC/MS |
|---|---|---|---|
| Example 6 | 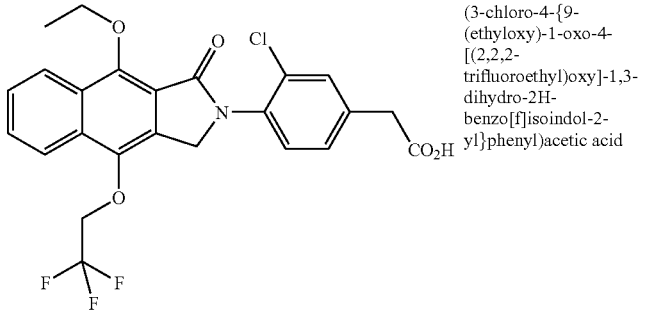 | (3-chloro-4-{9-(ethyloxy)-1-oxo-4-[(2,2,2-trifluoroethyl)oxy]-1,3-dihydro-2H-benzo[f]isoindol-2-yl}phenyl)acetic acid | Rt = 3.33 [MH]⁺494 |

Example 7

(4-{9-(Ethyloxy)-1-oxo-4-[(2,2,2-trifluoroethyl)oxy]-1,3-dihydro-2H-benzo[f]isoindol-2-yl}-3-fluorophenyl)acetic acid

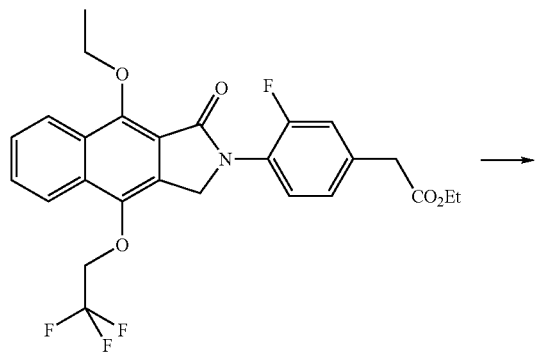

→

-continued

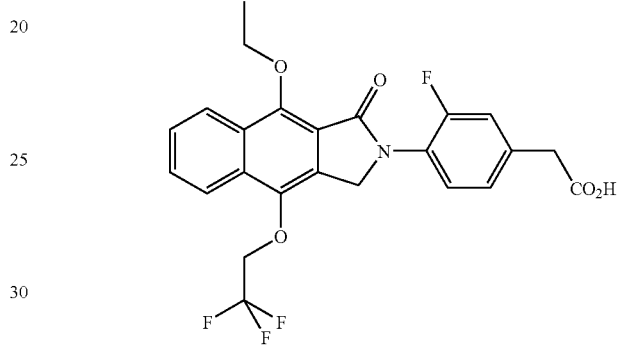

Ethyl (4-{9-(ethyloxy)-1-oxo-4-[(2,2,2-trifluoroethyl)oxy]-1,3-dihydro-2H-benzo[f]isoindol-2-yl}-3-fluorophenyl)acetate (0.118 g, 0.23 mmol) was heated to 100° C. in a 1:1 mixture of acetic acid:HCl (2N) (8 ml) for 1 hour. On addition of water, the resulting white solid was collected by filtration and washed with water (0.099 g, 0.21 mmol). LC/MS: Rt=3.25, [MH]⁺ 478.

The following compound was prepared in a similar manner (4-{9-(ethyloxy)-1-oxo-4-[(2,2,2-trifluoroethyl)oxy]-1,3-dihydro-2H-benzo[f]isoindol-2-yl}-3-fluorophenyl)acetic acid using the appropriate starting material.

| | | Name | LC/MS |
|---|---|---|---|
| Example 8 | 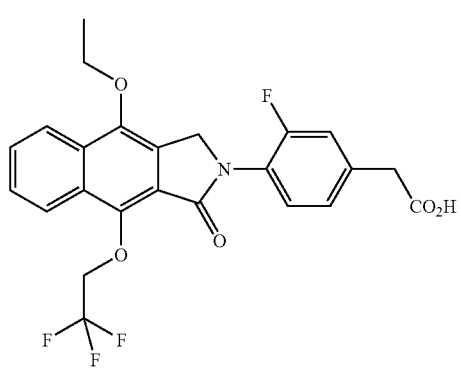 | (4-{4-(Ethyloxy)-1-oxo-9-[(2,2,2-trifluoroethyl)oxy]-1,3-dihydro-2H-benzo[f]isoindol-2-yl}-3-fluorophenyl)acetic acid | Rt = 3.24 [MH]⁺478 |

Biological Data

Studies were performed using HEK-293(T) cells expressing the recombinant human prostanoid $EP_4$ receptor (HEK-$EP_4$ cells). Cells were grown as a monolayer culture in DMEM-F12/F12 containing glutamax II (Gibco) and supplemented with 10% foetal bovine serum and 0.4 mg·ml-1 G418. HEK-$EP_4$ cells were pre-treated 24 hr and 30 mins prior to the experiment with 10 μM indomethacin and harvested using Versene containing 10 μM indomethacin. The cells were resuspended in assay buffer (DMEM:F12, 10 μM indomethacin and 200 μM IBMX) at $1 \times 10^6$ cells per ml and incubated for 20 min at 37° C. Thereafter, 50 μl of cells were added to 50 ul agonist (compound of Formula (I)) and incubated at 37° C. for 4 minutes before stopping reactions with 100 μl of 1% triton X-100. cAMP levels in the cell lysates were determined using a competition binding assay. In this assay the ability of cell lysates to inhibit 3H-cAMP (Amersham) binding to the binding subunit of protein kinase A was measured and cAMP levels were calculated from a standard curve. The data for each compound were expressed as a % of the response to a 10 nM maximal concentration of the standard agonist PGE2. For each compound the maximal response and concentration of compound causing 50% of its maximal response were calculated. Intrinsic activity is expressed relative to the maximal response to PGE2. Unless stated, reagents were purchased commercially from Sigma.

The examples of the present invention were tested in the above-mentioned assay and exhibited $pEC_{50}$ values of 6.5 or higher and intrinsic activities of 20% or higher.

What is claimed is:

1. An $EP_4$ receptor (prostaglandin E2 receptor type 4) agonist selected from the group consisting of:
    (3-chloro-4-{1,3-dioxo-4,9-bis[(2,2,2-trifluoroethyl)oxy]-1,3-dihydro-2H-benzo[f]isoindol-2-yl}phenyl)acetic acid;
    (3-chloro-4-{1-oxo-4,9-bis[(2,2,2-trifluoroethyl)oxy]-1,3-dihydro-2H-benzo[f]isoindol-2-yl}phenyl)acetic acid;
    (4-{4-(ethyloxy)-1,3-dioxo-9-[(2,2,2-trifluoroethyl)oxy]-1,3-dihydro-2H-benzo[f]isoindol-2-yl}-3-fluorophenyl)acetic acid;
    (3-chloro-4-{4-(ethyloxy)-1,3-dioxo-9-[(2,2,2-trifluoroethyl)oxy]-1,3-dihydro-2H-benzo[f]isoindol-2-yl}phenyl)acetic acid;
    (3-chloro-4-{4-(ethyloxy)-1-oxo-9-[(2,2,2-trifluoroethyl)oxy]-1,3-dihydro-2H-benzo[f]isoindol-2-yl}phenyl)acetic acid;
    (3-chloro-4-{9-(ethyloxy)-1-oxo-4-[(2,2,2-trifluoroethyl)oxy]-1,3-dihydro-2H-benzo[f]isoindol-2-yl}phenyl)acetic acid;
    (4-{9-(ethyloxy)-1-oxo-4-[(2,2,2-trifluoroethyl)oxy]-1,3-dihydro-2H-benzo[f]isoindol-2-yl}-3-fluorophenyl)acetic acid;
    (4-{4-(ethyloxy)-1-oxo-9-[(2,2,2-trifluoroethyl)oxy]-1,3-dihydro-2H-benzo[f]isoindol-2-yl}-3-fluorophenyl)acetic acid; and a pharmaceutically acceptable salt thereof.

2. The $EP_4$ receptor agonist of claim 1 selected from the group consisting of
    (4-{4-(ethyloxy)-1,3-dioxo-9-[(2,2,2-trifluoroethyl)oxy]-1,3-dihydro-2H-benzo[f]isoindol-2-yl}-3-fluorophenyl)acetic acid;
    (4-{9-(ethyloxy)-1-oxo-4-[(2,2,2-trifluoroethyl)oxy]-1,3-dihydro-2H-benzo[f]isoindol-2-yl}-3-fluorophenyl)acetic acid;
    (4-{4-(ethyloxy)-1-oxo-9-[(2,2,2-trifluoroethyl)oxy]-1,3-dihydro-2H-benzo[f]isoindol-2-yl}-3-fluorophenyl)acetic acid; and
    a pharmaceutically acceptable salt thereof.

3. The $EP_4$ receptor agonist of claim 2 which is (4-{4-(ethyloxy)-1,3-dioxo-9-[(2,2,2-trifluoroethyl)oxy]-1,3-dihydro-2H-benzo[f]isoindol-2-yl}-3-fluorophenyl)acetic acid.

4. A pharmaceutical composition comprising a compound according to claim 1, or its pharmaceutically acceptable salt thereof and one or more acceptable carriers or diluents.

5. A pharmaceutical composition according to claim 4, comprising one or more additional therapeutic agents, wherein said therapeutic agents are selected from the group consisting of 5-lipoxygenase inhibitors, NSAIDs, leukotriene receptor antagonists, DMARDs, $EP_2$ receptor ligands, and cannabanoid receptor agonists.

6. A method of treating a human or animal subject suffering from a condition which is mediated by the action, or by loss of action, of $PGE_2$ (prostaglandin E2) at $EP_4$ receptors which comprises administering to said subject an effective amount of a compound according to claim 1, wherein said condition is a pain, inflammatory, immunological, bone, neurodegenerative or renal disorder.

7. The method according to claim 6 wherein the inflammatory disorder is a lung disorder.

8. The method according to claim 7 wherein the lung disorder is COPD or asthma.

* * * * *